United States Patent
Okuyama et al.

(10) Patent No.: US 9,120,723 B2
(45) Date of Patent: *Sep. 1, 2015

(54) MODULATOR

(71) Applicant: CANBEX THERAPEUTICS LIMITED, London (GB)

(72) Inventors: Masahiro Okuyama, Osaka (JP); David Selwood, London (GB); Cristina Visintin, London (GB); David Baker, London (GB); Gareth Pryce, London (GB)

(73) Assignee: CANBEX THERAPEUTICS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/654,942

(22) Filed: Oct. 18, 2012

(65) Prior Publication Data

US 2013/0123356 A1 May 16, 2013

Related U.S. Application Data

(63) Continuation of application No. 12/707,812, filed on Feb. 18, 2010, now Pat. No. 8,293,796, which is a continuation of application No. 10/590,064, filed as application No. PCT/GB2005/000605 on Feb. 21, 2005, now Pat. No. 7,696,382.

(30) Foreign Application Priority Data

Feb. 20, 2004 (GB) .................................. 0403864.2

(51) Int. Cl.
| | |
|---|---|
| *C07C 233/00* | (2006.01) |
| *C07C 255/44* | (2006.01) |
| *C07C 69/76* | (2006.01) |
| *C07C 233/11* | (2006.01) |
| *C07C 233/65* | (2006.01) |
| *C07C 233/66* | (2006.01) |
| *C07C 233/69* | (2006.01) |
| *C07C 235/42* | (2006.01) |
| *C07C 235/78* | (2006.01) |
| *C07C 235/84* | (2006.01) |
| *C07C 237/32* | (2006.01) |
| *C07C 237/38* | (2006.01) |
| *C07C 237/42* | (2006.01) |

(Continued)

(52) U.S. Cl.
CPC .............. *C07C 255/44* (2013.01); *C07C 69/76* (2013.01); *C07C 69/78* (2013.01); *C07C 233/11* (2013.01); *C07C 233/65* (2013.01); *C07C 233/66* (2013.01); *C07C 233/69* (2013.01); *C07C 235/42* (2013.01); *C07C 235/78* (2013.01); *C07C 235/84* (2013.01); *C07C 237/32* (2013.01); *C07C 237/38* (2013.01); *C07C 237/42* (2013.01); *C07C 255/41* (2013.01)

(58) Field of Classification Search
CPC ............................ A61K 31/165; C07C 233/15
USPC .......... 564/123, 152, 155, 156, 158; 514/613, 514/617
See application file for complete search history.

(56) References Cited

U.S. PATENT DOCUMENTS

| 4,948,796 A | 8/1990 | Hiraiwa et al. |
|---|---|---|
| 5,342,971 A | 8/1994 | Herlt et al. |
| 6,689,883 B1 * | 2/2004 | Boyer et al. .................. 544/235 |

(Continued)

FOREIGN PATENT DOCUMENTS

| DE | 3906920 C2 * | 7/1998 |
|---|---|---|
| EP | 0 146 920 A2 | 7/1985 |

(Continued)

OTHER PUBLICATIONS

Usmani et al, Drug Metabolism and Disposition (2002), 30(3), 289-294.*

Matsuda et al, Pesticide Biochemistry and Physiology (1989), 35(3), 300-14.*

Izzo et al, "Central and peripheral cannabinoid modulation of gastrointestinal transit in physiological states or during the diarrhoea induced by Croton oil", British Journal of Pharmacology, vol. 129, 2000, pp. 1627-1632.

Sarna et al, "Function and regulation of colonic contractions in health and disease" in Johnson L.R.: 'Physiology of the Gastrointestinal Tract', 2006, Academic Press, Fourth Edition, pp. 965-993.

(Continued)

*Primary Examiner* — Sudhakar Katakam

(74) *Attorney, Agent, or Firm* — Nixon & Vanderhye P.C.

(57) ABSTRACT

The present disclosure relates to a compound of formula (I), or a pharmaceutically acceptable salt thereof, wherein Z is selected from OH, $NHCH_2CH_2F$, $NHCH(Me)CH_2OH$ and $NHCH_2CH_2OH$; X is an alkylene, alkenylene, or alkynylene group, each of which may be optionally substituted by one or more substituents selected from alkyl, COOH, $CO_2$-alkyl, alkenyl, CN, $NH_2$, hydroxy, halo, alkoxy, $CF_3$ and nitro; Y is a polar functional group selected from OH, $NO_2$, CN, $COR^3$, $COOR^3$, $NR^3R^4$, $CONR^3R^4$, $SO_3H$, $SO_2$—$R^3$, $SO_2NR^3R^4$ and $CF_3$, where each of $R^3$ and $R^4$ is independently H or a hydrocarbyl group; A is phenyl or pyridyl; and B is $(CH_2)_n$ where n is 0; with the proviso that: (i) when A is phenyl, and Z is OH, X—Y is other than C≡C—$(CH_2)_2CO_2H$, C≡C—$(CH_2)_2CO_2Me$, $(CH_2)_4CO_2H$. Uses of such compounds as medicaments for the treatment of a muscular disorder, a gastrointestinal disorder, or for controlling spasticity or tremors are provided.

17 Claims, 3 Drawing Sheets

Figure 1:
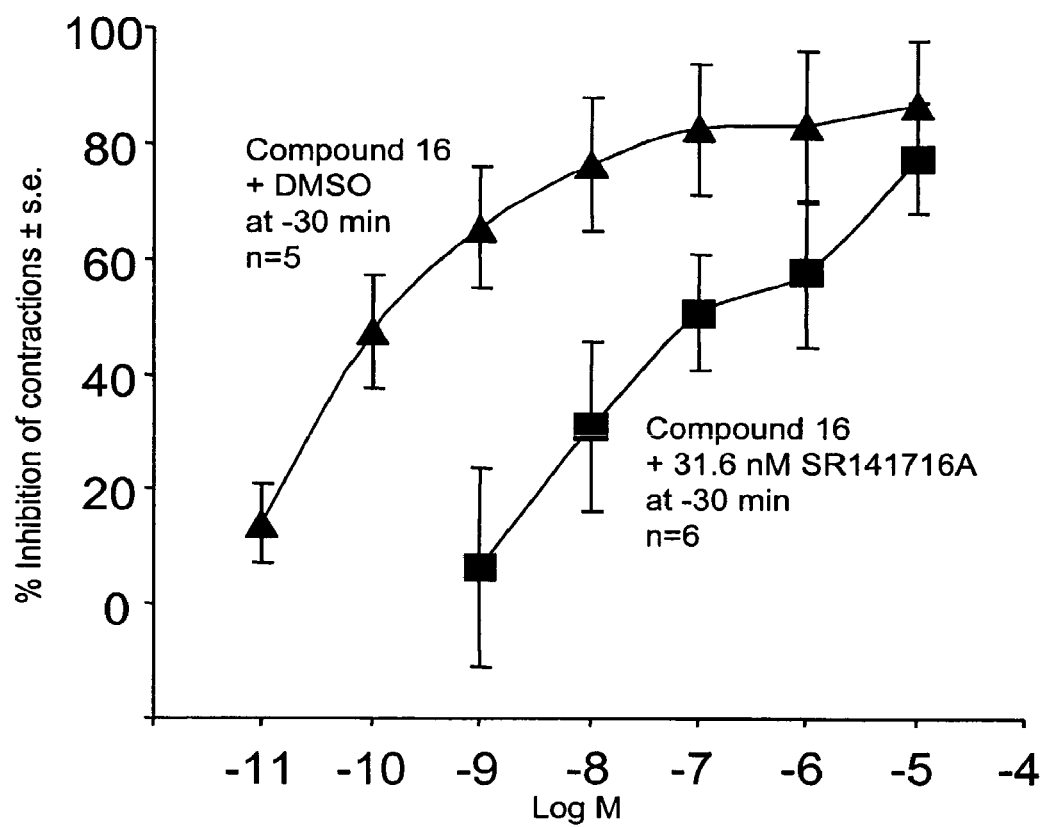

(51) Int. Cl.
C07C 255/41 (2006.01)
C07C 69/78 (2006.01)

(56) References Cited

U.S. PATENT DOCUMENTS

| | | | |
|---|---|---|---|
| 7,696,382 B2* | 4/2010 | Okuyama et al. ............ 564/154 |
| 2003/0191069 A1 | 10/2003 | Inaba et al. |
| 2008/0114062 A1 | 5/2008 | Okuyama et al. |
| 2008/0262011 A1 | 10/2008 | Selwood |
| 2010/0144876 A1 | 6/2010 | Okuyama et al. |

FOREIGN PATENT DOCUMENTS

| | | |
|---|---|---|
| EP | 0 329 464 A2 | 8/1989 |
| GB | 2 196 629 A | 5/1988 |
| HU | 2001004831 A1 * | 8/2003 |
| JP | 01-316363 | 12/1989 |
| JP | 2001-513529 | 9/2001 |
| WO | 00/16756 | 3/2000 |
| WO | WO 0078708 A1 * | 12/2000 |
| WO | WO 0103661 A1 * | 1/2001 |
| WO | WO 03/004096 A2 | 1/2003 |
| WO | WO 03040096 A2 | 5/2003 |
| WO | WO 03070182 A2 * | 8/2003 |
| WO | 03/091204 A1 | 11/2003 |
| WO | WO 03/091189 | 11/2003 |
| WO | 03/106420 A1 | 12/2003 |
| WO | WO 2004/017920 | 3/2004 |
| WO | WO 2004/024939 A2 | 3/2004 |
| WO | 2004/074224 A1 | 9/2004 |
| WO | 2004/078180 A2 | 9/2004 |

OTHER PUBLICATIONS

Snape, "Colonic Transit and Motility", 'Colonic Diseases', 2003, T.R. Koch, Humana Press Inc., Totowa, NJ, pp. 335-343.
Korolkiewicz et al, "Differential salutary effects of non-selective and selective COX-2 inhibitors in postoperative ileus in rats", Journal of Surgical Research, vol. 109, 2003, pp. 161-169.
Stubberöd et al, "The effect of cisapride and ranitidine as monotherapies and in combination in the treatment of uncomplicated gastric ulceration", Scand. J. Gastroenterol, No. 30, 1995, pp. 106-110.
Database CA [Online] Chemical Abstracts Service, Columbus, Ohio, US; Takado, Toru et al: "Novel imidazoquinolinones and their use as antiparkinsonian agents" XP002555427 retrieved from STN Database accession No. 140:210794 & JP 2004 059538 A (Sumitomo Pharmaceutical Co., Ltd., Japan) Feb. 26, 2004.
Database CA [Online] Chemical Abstracts Service, Columbus, Ohio, US; Takeshita, Hiroshi et al: "Polymerizable unsaturated group-containing N-substituted amides for bisphenol A-free dental materials" XP002555428 retrieved from STN Database accession No. 133:125328 & JP 2000 204069 A (Tokuyama Corp., Japan) Jul. 25, 2000.
Database Beilstein [Online] Beilstein Institute for Organic Chemistry, Frankfurt-Main, DE; XP002555432 Database accession No. 7777227 (BRN)—& Varney, M.Palmer, C. et al.: "Protein Structure—Based Design, Synthesis, and Biological Evaluation of 5-Thia-2,6-diamino-4(3H)-oxopyrimides: potent Inhibitors of Glycinamide Ribonucleotide Transformylase with Potent Cell Growth Inhibition" Journal of Medicinal Chemistry, vol. 40, No. 16, 1997, pp. 2502-2524, XP002555503.
Database Beilstein [Online] Beilstein Institute for Organic Chemistry, Frankfurt-Main, DE; XP002555433 Database accession No. 6932805 (BRN) & McDowell, R.; Black B. et al.: Journal of the American Chemical Society, vol. 116, No. 12, 1994, pp. 5077-5083.
Database Beilstein [Online] Beilstein Institute for Organic Chemistry, Frankfurt-Main, DE; XP002555434 Database accession No. 6930766 (BRN) & McDower.; B. et al.: Journal of American Chemical Society, vol. 116, No. 12, 1994, pp. 5077-5083.
Database Beilstein [Online] Beilstein Institute for Organic Chemistry, Frankfurt-Main, DE; XP002555435 Database accession No. 7776039 (BRN) & Varney, M; Palmer, C. et al.: Journal of Medicinal Chemistry, vol. 40, No. 16, 1997, pp. 2502-2542.
Vrasidas et al, "Synthesis and Cholera Toxin Binding Properties of a Lactose-2-aminothiazoline Conjugate", Pieters et al., Organic Letters, 2002, vol. 4, No. 10, pp. 1807-1808.
Berglund et al, "Development of a Novel Class of Monocyclic and Bicyclic Alkyl Amides that Exhibit $CB_1$ and $CB_2$ Cannabinoid Receptor Affinity and Receptor Activation", Drug Design and Discovery, 2000, vol. 16, pp. 281-294.
Rodriguez et al, "A Selective Method for the Preparation of Aliphatic Methyl Esters in the Presence of Aromatic Carboxylic Acids", Tetrahedron Letters, 1998, vol. 39, No. 47, pp. 8563-8566.
International Search Report of PCT/GB2005/000605, mailed Aug. 5, 2005.
Database CA Online!, Chemical Abstracts Service, Oshima et al; "Synthesis and antiallergic activity of 11-(aminoalkylidene)-6,11-dihydrodibenz'b,e!oxepin derivatives", XP002333556, Database accession No. 1992:255459.
Journal of Medicinal Chemistry, 35(11), 2074-84, JMCMAR; ISSN:0022-2623, 1992.
Database CA Online!, Ishikawa et al., "Insulation film materials, varnishes containing them, polyoxazole-bases microporous films with low moisture absorption manufactured from them, and semiconductor devices using them", XP-002333557, Database accession No. 2004:1987.
Database CA Online!, Oren et al., Photochemical Studies, Part 21, "Homoconjugated ketones with extended and enantiospecific photochemical transformation of methyl 7-oxospiro[5.5]undeca-1, 3- and -2,4-diene-2-carboxylate", XP002333558, Database accession No. 1993:580433.
Database CA 'Online!, Chemical Abstracts Service, Bergman et al, "Chemical stability of a prostacyclin analog due to the absence of intramolecular catalysis", XP002333559, Database accession No. 1988:221428.
Journal of Organic Chemistry, 53(11), 2548-52 Coden: Joceah; ISSN: 0022-3263, 1988.
Database Beilstein 'Online! XP002333560, accession No. BRN 7478893, Nov. 12, 1996.
Database Beilstein 'Online! XP002333561, accession No. BRN 7705788, Nov. 18, 1997.
Database Beilstein 'Online! XP002333562, accession No. BRN 7704940, Nov. 18, 1997.
Database Beilstein 'Online! XP002333563, accession No. BRN 7434441, Aug. 9, 1996.
Database Beilstein 'Online! XP002333564, accession No. BRN 3414970, Feb. 15, 1990.
Database Beilstein 'Online! XP002333565, accession No. BRN 2803986, Jul. 11, 1989.
Database Beilstein 'Online! XP002333566, accession No. BRN 7478893, Nov. 12, 1996.
Database Beilstein 'Online! XP002333567, accession No. BRN 2576796, Jul. 5, 1989.
Database Beilstein 'Online! XP002333568, accession No. BRN 2093695, Jun. 29, 1989.
Database Beilstein 'Online! XP002333569, accession No. BRN 4862361, May 4, 1993.
Database Beilstein 'Online! XP002333570, accession No. BRN 2720943, Jul. 11, 1989.
Database Beilstein 'Online! XP002333571, accession No. BRN 2578485, Jul. 5, 1989.
Database Beilstein 'Online! XP002333572, accession No. BRN 9028430, Apr. 29, 2002.
Database Beilstein 'Online! XP002333573, accession No. BRN 8102389, May 6, 1999.
Database Beilstein 'Online! XP002333574, accession No. BRN 7884890, Jul. 15, 1998.
Database Beilstein 'Online! XP002333575, accession No. BRN 7884829, Jul. 15, 1998.
Database Beilstein 'Online! XP002333576, accession No. BRN 7595800, Apr. 28, 1997.
Database Beilstein 'Online! XP002333577, accession No. BRN 7157925, Jul. 28, 1995.

(56) References Cited

OTHER PUBLICATIONS

Database Beilstein 'Online! XP002333578, accession No. BRN 5989239, Jul. 22, 1993.
Database Beilstein 'Online! XP002333579, accession No. BRN 4000587, Mar. 19, 1991.
Database Beilstein 'Online! XP002333580, accession No. BRN 945015, Nov. 28, 1988.
Database Beilstein 'Online! XP002333583, accession No. BRN 433087, Nov. 28, 1988.
Database Beilstein 'Online! XP002333584, accession No. BRN 2381895, Jul. 5, 1989.
Wiley et al, "Resorcinol Derivatives: A Novel Template for the Development of Cannabinoid $CB_1/CB_2$ and $CB_2$-Selective Agonists", The Journal of Pharmacology and Experimental Therapeutics, 2002, vol. 301, No. 2, pp. 679-689.
Mahadevan et al, "Novel Cannabinol Probes for CB1 and CB2 Cannabinoid Receptors", J. Med. Chem. 2000, 43, 3778-3785.
Zhou et al, "10-Hydroxy-10,9-boroxarophenanthrenes: Versatile Synthetic Intermediates to 3,4-Benzocoumarins and Triaryls", J. Org. Chem. 2004, 69, 5147-5149.
Ming-Yuan et al, "Ruthenium-Catalyzed Cyclization of Alkyne-Epoxide Functionalities through Alternation of the Substituent and Structural Skeleton of Epoxides", J. Org. Chem. 2004, 69, 7770-7704.
Onaka et al, "Desulfurization Characteristics of Thermophilic *Paenibacillus* sp. Strain A11-2 against Asymmetrically Alkylated Dibenzothiophenes", Journal of Bioscience and Bioengineering, vol. 92, No. 2, 193-196, 2001.
Gareau et al, "Structure Activity Relationships of Tetrahydrocannabinol Analogues on Human Cannabinoid Receptors", Bioorganic & Medicinal Chemistry Letters, vol. 6, No. 2, pp. 189-194, 1996.
Claims filed Jun. 20, 2007 in copending U.S. Appl. No. 11/793,476.
Written Opinion of the International Searching Authority for Application No. PCT/GB2005/004990, dated Jun. 26, 2007.
Freeman et al, Hexamethylene-1,6-bis(tertiary amine), Journal of the American Chemical Society (1956), 78, 4077-81.
McDowell et al, "From Peptide to Non-Peptide. 2. The de Novo Design of Potent, Non-peptidal Inhibitors of Platelet Aggregation Based on a Benzodiazepinedione Scaffold", Journal of the American Chemical Society, 116(12), 5077-5083, 1994.
Caldwell et al, "Cardiovascular effects of KM-13, a new, orally effective, cardiotonic sympathomimetic amine", Journal of Cardiovascular Pharmacology, 9(3), 375-384, 1987.
Database Beilstein 'Online! XP002333580, accession No. BRN 945016, Nov. 28, 1988.
European Search Report dated Mar. 3, 2010 mailed in EP09012361.3 (UCL Business PLC).

\* cited by examiner

MODULATOR

This application is a continuation of application Ser. No. 12/707,812 (U.S. Patent Application Publication No. 2010-0144876 A1), filed Feb. 18, 2010 (issued as U.S. Pat. No. 8,293,796), which is a continuation of application Ser. No. 10/590,064, filed Oct. 2, 2007 (issued as U.S. Pat. No. 7,696,382), which is a U.S. national phase of International Application No. PCT/GB2005/000605, filed 21 Feb. 2005, which designated the U.S. and claims benefit of GB 0403864.2, filed 20 Feb. 2004, the entire contents of each of which is hereby incorporated by reference in this application.

The present invention relates to compounds capable of modulating cannabinoid receptors.

BACKGROUND TO THE INVENTION

There has recently been renewed interest in the therapeutic uses of medical *cannabis* and synthetic cannabinoids, such as $\Delta^9$-tetrahydrocannabinol (THC) [1], the active component of *cannabis*.

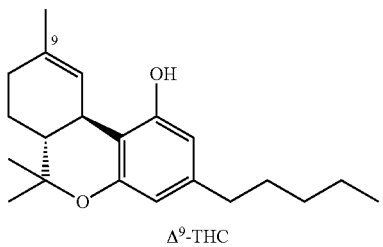

Δ⁹-THC [1]

THC may be therapeutically beneficial in several major areas of medicine including control of acute and in particular chronic/neuropathic pain, nausea, anorexia, AIDS, glaucoma, asthma and in multiple sclerosis [Baker, D. et al, *Nature* 2000, 404, 84-87; Baker, D. et al, *FASEB J.* 2001, 15, 300-302; Schnelle, M. et al, *Forsch. Komplementarmed.* 1999, 6 *Suppl* 3, 28-36].

A number of cannabinoid ligands have been reported in the literature. Broadly speaking, cannabinoid ligands may be divided into three main groups consisting of (i) classical cannabinoids, such as (−)-$\Delta^9$-tetrahydrocannabinol, $\Delta^9$-THC [1] and CP55,940 [9]; (ii) endocannabinoids, such as anandamide [2] and 2-arachidonoyl glycerol [3]; and (iii) non-classical heterocyclic analogues typified by heterocycles such as WIN 55,212 [7] and the selective CB₁ antagonist SR141716A [8] [Pertwee, R. G., *Pharmacology & Therapeutics* 1997, 74, 129-180]. Conformationaily restricted anandamide analogues have also been reported [Berglund, B. A. et al, *Drug Design and Discovery* 2000, 16, 281-294]. To date, however, the therapeutic usefulness of cannabinoid drugs has been limited by their undesirable psychoactive properties.

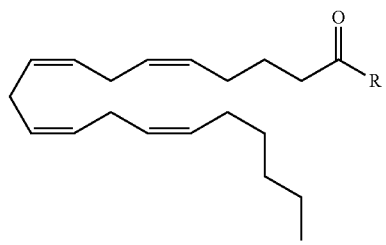

[2] anandamide, R = NHCH₂CH₂OH
[3] arachidonylglycerol R = OCH(CH₂OH)₂

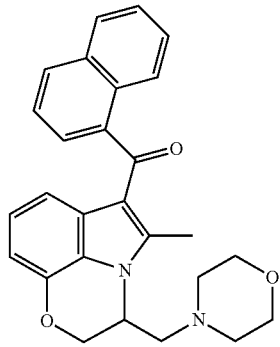

WIN55,212 [7]

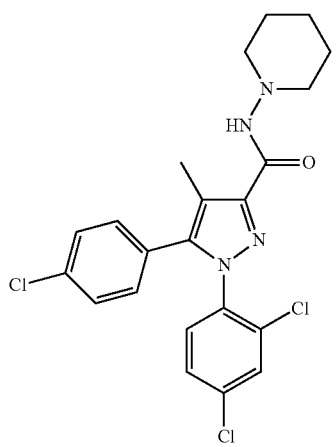

SR141716A [8]

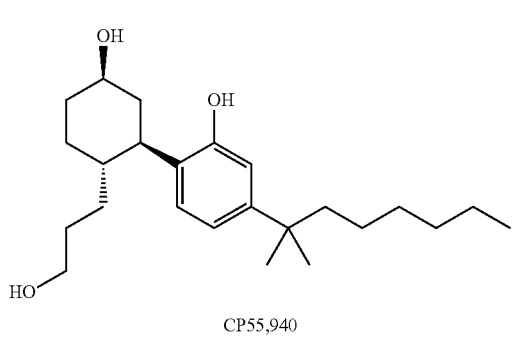

CP55,940 [9]

Cannabinoids are known to modulate nociceptive processing in models of acute, inflammatory and neuropathic pain [Pertwee, R. G., *Prog. Neurobiol.* 2001, 63, 569-611]. More specifically, research has centred on the role of cannabinoids in models of neuropathic hyperalgesia [Herzberg, U. et al, Neurosci. Lett. 1997, 221, 157-160] and inflammatory hyperalgesia [Richardson, J. D., Pain 1998, 75, 111-119; Jaggar, S. I. et al, Pain 1998, 76, 189-199; Calignano, A. et al, Nature 1998, 394, 277-281; Hanus, L. et al, Proc. Natl. Acad. Sci. U.S.A. 1999, 96, 14228-14233]. It has also been suggested that cannabinoid receptor expression and the level of endogenous cannabinoids may change during inflammation and hyperalgesia [Pertwee, R. G., Prog. Neurobiol. 2001, 63, 569-611]. The cannabinoid signaling system is thought to involve two cloned cannabinoid receptors ($CB_1$ and $CB_2$), endocannabinoid ligands such as anandamide [2] and 2-arachidonoyl glycerol [3], and an endocannabinoid degradation system [Howlett, A. C. et al, International Union of Pharmacology XXVII, Pharmacol. Rev. 2002, 54, 161-202; Pertwee, R. G., Pharmacology of cannabinoid receptor ligands. Curr. Med. Chem. 1999, 6, 635-664].

One important function of the cannabinoid system is to act as a regulator of synaptic neurotransmitter release [Kreitzer, A. C. et al, Neuron 2001, 29, 717-727; Wilson, R. I. et al, Neuron 2001, 31, 453-462]. $CB_1$ is expressed at high levels in the CNS, notably the globus pallidus, substantia nigra, cerebellum and hippocampus [Howlett, A. C., Neurobiol. Dis. 1998, 5, 405-416]. This is consistent with the known adverse effects of cannabis on balance and short-term memory processing [Howlett, A. C. et al, International Union of Pharmacology XXVII, Pharmacol. Rev. 2002, 54, 161-202]. $CB_2$ is expressed by leucocytes and its modulation does not elicit psychoactive effects; moreover it does not represent a significant target for symptom management where the majority of effects are $CB_1$ mediated.

Although many cannabinoid effects are centrally-mediated by receptors in the CNS [Howlett, A. C. et al, International Union of Pharmacology XXVII, Pharmacol. Rev. 2002, 54, 161-202], it is understood that peripheral CB receptors also play an important role, particularly in pain and in the gastrointestinal tract. For example, $CB_1$ is also expressed in peripheral tissues, such as in dorsal root ganglia, peripheral nerves and neuromuscular terminals, thereby allowing neurotransmission to be regulated outside the CNS [Pertwee, R. G., Life Sci. 1999, 65, 597-605]. Accordingly, therapeutic activity in conditions such as those involving pain [Fox, A. et al, Pain 2001, 92, 91-100] or gut hypermotility, may be located in non-CNS sites. To date, however, research into the peripheral cannabinoid system has been hampered by the lack of pharmacological agents that selectively target peripheral receptors over those of the CNS.

In order to eliminate adverse psychoactive effects, it is desirable to exclude cannabinoid agonists from the CNS. There are two established methods for CNS exclusion of small molecule agents. Firstly, one method involves excluding substances from the CNS by carefully controlling their physicochemical properties so as to prevent them crossing the blood brain barrier (BBB). The BBB is formed by brain endothelial cells, with tight intercellular junctions and little fenestration [Tamai, I. et al, J. Pharm. Sci. 2000, 89, 1371-1388]. Consequently, substances must enter the brain either by passive diffusion across plasma membranes or by active transport mechanisms. The BBB thus forms an effective barrier to many peripherally circulating substances.

An alternative method of excluding compounds from the brain is to incorporate structural features which enable them to be actively pumped across the BBB. One such example is the opioid agonist loperamide; although lipophilic, loperamide contains structural features recognized by the p-glycoprotein transporter (MDR1) that allow it to be actively pumped across the blood brain barrier. [Wandel, C. et al, Anesthesiology 2002, 96, 913-920; Seelig, A. et al, Eur. J. Pharm. Sci. 2000, 12, 31-40].

The present invention seeks to provide new cannabinoid receptor modulators. More particularly, the invention seeks to provide cannabinoid receptor modulators that alleviate and/or eliminate some of the disadvantages commonly associated with prior art modulators, for example undesirable psychoactive side effects. More specifically, though not exclusively, the invention seeks to provide modulators that selectively target peripheral cannabinoid receptors.

STATEMENT OF INVENTION

A first aspect of the invention relates to a compound of formula I, or a pharmaceutically acceptable salt thereof,

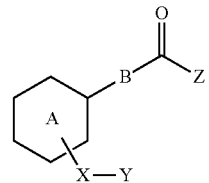

wherein

Z is $OR^1$ or $NR^1R^2$ wherein each of $R^1$ and $R^2$ is independently H, or a hydrocarbyl group;

X is an alkylene, alkenylene, or alkynylene group, each of which may be optionally substituted by one or more substituents selected from alkyl, COOH, $CO_2$-alkyl, alkenyl, CN, $NH_2$, hydroxy, halo, alkoxy, $CF_3$ and nitro;

Y is a polar functional group selected from OH, $NO_2$, CN, $COR^3$, $COOR^3$, $NR^3R^4$, $CONR^3R^4$, $SO_3H$, $SO_2$—$R^3$, $SO_2NR^3R^4$ and $CF_3$, where each of $R^3$ and $R^4$ is independently H or a hydrocarbyl group;

A is an aryl or heteroaryl group, each of which may be optionally substituted; and B is $(CH_2)_n$ where n is 0, 1, 2, 3, 4 or 5;

with the proviso that:

(i) when A is phenyl, n is 0, and Z is OH, X—Y is other than meta-C≡C—$(CH_2)_2CO_2H$, meta-C≡C—$(CH_2)_2OH$, meta-C≡C—$(CH_2)_2CO_2Me$, meta-$(CH_2)_4CO_2H$, ortho-$CH_2CO_2H$, ortho-$(CH_2)_2CO_2H$ and ortho-$(CH_2)_4CO_2H$; and (ii) when A is phenyl, n is 0, and Z is OMe, X—Y is other than meta-C≡C—$(CH_2)_4OH$.

Advantageously, the compounds of the present invention preferably exhibit improved aqueous solubility and/or decreased lipophilicity compared to prior art cannabinoid receptor modulators.

A second aspect of the invention relates to the use of a compound of formula Ia, or a pharmaceutically acceptable salt thereof,

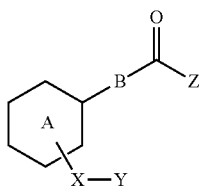

Ia wherein

Z is OR$^1$ or NR$^1$R$^2$ wherein each of R$^1$ and R$^2$ is independently H, or a hydrocarbyl group;

X is an alkylene, alkenylene, or alkynylene group, each of which may be optionally substituted;

Y is a polar functional group;

A is an aryl or heteroaryl group, each of which may be optionally substituted; and B is (CH$_2$)$_n$ where n is 0, 1, 2, 3, 4 or 5.

in the preparation of a medicament for treating a muscular disorder.

A third aspect of the invention relates to the use of a compound of formula Ia, or a pharmaceutically acceptable salt thereof, as defined above in the preparation of a medicament for controlling spasticity and tremors.

A fourth aspect of the invention relates to the use of a compound of formula Ia, or a pharmaceutically acceptable salt thereof, as defined above in the preparation of a medicament for treating a gastrointestinal disorder.

A fifth aspect of the invention relates to a pharmaceutical composition comprising a compound of formula I as defined above admixed with a pharmaceutically acceptable diluent, excipient or carrier.

A sixth aspect of the invention relates to the use of a compound of formula Ia, or a pharmaceutically acceptable salt thereof, in an assay for identifying further compounds capable of modulating cannabinoid receptor activity.

DETAILED DESCRIPTION

Cannabinoid

A cannabinoid is an entity that is capable of binding to a cannabinoid receptor, in particular CB1 and/or CB2. Typical cannabinoids include the 30 or so derivatives of 2-(2-isopropyl-5-methylphenyl)-5-pentylresorcinol that are found in the Indian hemp, *Cannabis sativa*, among which are those responsible for the narcotic actions of the plant and its extracts. Examples of cannabinoids are cannabidiol, cannabinol, trans-$\Delta^9$-tetrahydrocannabinol, trans-$\Delta^8$-tetrahydrocannabinol, and $\Delta^9$-tetrahydro-cannabinolic acid. Other examples of cannabinoids include anandamide, methanandamide and R(+)WIN55,212.

Endocannabinoid

This term means a cannabinoid that exists naturally in the body—as opposed to an exogeneously supplied cannabinoid. Endocannabinoids are discussed by Di Marzo (1998) Biochimica et Biophysica Acta vol 1392 pages 153-175 (the contents of which are incorporated herein by reference). An example of an endocannabinoid is anandamide. Teachings on this entity and anandamide amidase may be found in U.S. Pat. No. 5,874,459. This document teaches the use of anandamide amidase inhibitors as analgesic agents.

Cannabinoid Receptor

A cannabinoid receptor is any one or more of several membrane proteins that bind cannabinol and structurally similar compounds and mediate their intracellular action.

Two receptors for the psychoactive ingredient of marijuana $\Delta^9$-tetrahydrocannabinol (THC), the CB1 and CB2 cannabinoid receptors, have been found (Pertwee 1997 Pharmacol Ther vol 74 129-180). Both of these receptors are seven-transmembrane-domain G-protein-coupled receptors. CB$_1$ receptors are found in the brain and testis. CB$_2$ receptors are found in the spleen and not in the brain.

For both types of receptor arachidonoylethanolamide (anandamide) is a putative endogenous ligand and both types are negatively coupled to adenylate cyclase decreasing intracellular cyclic AMP levels. Examples of sequences for such receptors are from *Mus musculus*—and include: CB1, database code CB1R_MOUSE, 473 amino acids (52.94 kDA); CB2, database code CB2R_MOUSE, 347 amino acids (38.21 kDa). More details on CB1 and CB2 now follow.

Cannabinoid Receptor 1 (CB$_1$ or CNR1)

Background teachings on CB$_1$ have been presented by Victor A. McKusick et al on http://www.ncbi.nlm.nih.gov/Omim. The following information concerning CB$_1$ has been extracted from that source.

The cannabinoids are psychoactive ingredients of marijuana, principally delta-9-tetrahydrocannabinol, as well as the synthetic analogs Matsuda et al [*Nature* 346: 561-564, 1990] cloned a cannabinoid receptor from a rat brain. Using a cosmid clone of the entire coding sequence of the human gene, Modi and Bonner [Abstract, *Cytogenet. Cell Genet.* 58: 1915 only, 1991] mapped the human CNR locus to 6q14-q15 by in situ hybridization. Gerard et al. [*Biochem. J.* 279: 129-134,1991]isolated a cDNA encoding a cannabinoid receptor from a human brain stem cDNA library. The deduced amino acid sequence encoded a protein of 472 residues which shared 97.3% identity with the rat cannabinoid receptor cloned by Matsuda et al [ibid, 1990]. They provided evidence for the existence of an identical cannabinoid receptor expressed in human testis. Hoehe et al [*New Biologist* 3: 880-885, 1991] determined the genomic localization of the CNR gene by combination of genetic linkage mapping and chromosomal in situ hybridization. Close linkage was suggested with CGA which is located at 6q21.1-q23; maximum lod=2.71 at theta=0.0. Moreover, CNR was linked to markers that define locus D6Z1, a sequence localized exclusively to centromeres of all chromosomes and enriched on chromosome 6. Ledent et al [*Science* 283: 401-404, 1999] investigated the function of the central cannabinoid receptor (CB1) by disrupting the gene in mice. Mutant mice did not respond to cannabinoid drugs, demonstrating the exclusive role of CB1 in mediating analgesia, reinforcement, hypothermia, hypolocomotion, and hypotension.

Cannabinoid Receptor 2 (CB2 or CNR2)

Background teachings on CB2 have been presented by Victor A. McKusick et al on http://www.ncbi.nlm.nih.gov/Omim. The following information concerning CB2 has been extracted from that source.

In addition to its renowned psychoactive properties, marijuana, or its major active cannabinoid ingredient, delta-9-tetrahydrocannabinol, exerts analgesic, antiinflammatory, immunosuppressive, anticonvulsive, and antiemetic effects as well as the alleviation of intraocular pressure in glaucoma. The G protein-coupled cannabinoid receptor-1 (CNR1; 114610), which is expressed in brain but not in the periphery, apart from low levels in testis, does not readily account for the nonpsychoactive effects of cannabinoids.

Using PCR with degenerate primers to screen a promyelocytic leukemia cell cDNA library [Munro, *Nature* 365: 61-65, 1993] obtained a cDNA encoding CNR2, which the authors called CX5. Sequence analysis predicted that the deduced 360-amino acid 7-transmembrane-spanning protein has 44% amino acid identity with CNR1 overall and 68% identity with the transmembrane residues proposed to confer ligand specificity. Binding analysis determined than CNR2 encodes a high-affinity receptor for cannabinoids, with higher affinity than CNR1 for cannabinol. Northern blot analysis revealed that the expression of 2.5- and 5.0-kb transcripts in the HL60 myeloid cell line increases on myeloid, or granulocyte, differentiation. Using the rat CX5 homolog, Munro [1993, ibid] found that the 2.5-kb transcript is expressed in spleen but not in brain, kidney, lung, thymus, liver, or nasal epithelium. In situ hybridization analysis demonstrated expression in splenic marginal zones. PCR analysis detected CNR2 expression in purified splenic macrophages but not in CD5+ T cells. Munro [1993, ibid] speculated that the location of CNR2 suggests that its endogenous ligand should have an immunomodulatory role. The International Radiation Hybrid Mapping Consortium mapped the CNR2 gene to chromosome (stSG90).

Compounds

As mentioned hereinabove, the compounds of the present invention preferably exhibit improved aqueous solubility and/or decreased lipophilicity compared to prior art cannabinoid modulators. Preferably, the compounds of the invention do not cross the blood-brain barrier to any substantial extent.

The present invention relates to compounds of formula I, Ia, Ib and Ic as defined herein.

As used herein, the term "hydrocarbyl" refers to a group comprising at least C and H that may optionally comprise one or more other suitable substituents. Examples of such substituents may include hydroxy, halo-, alkoxy-, nitro-, an alkyl group, or a cyclic group. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon. Preferably, the hydrocarbyl group is an alkyl group, an alkenyl, group, an aryl group, or a cycloalkyl group, each of which may be optionally substituted. More preferably, the hydrocarbyl group is alkyl, alkenyl, cycloalkyl or phenyl.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-10}$ alkyl group, more preferably still, a $C_{1-6}$ alkyl group. Particularly preferred alkyl groups include, for example, methyl, ethyl, propyl, isopropyl, butyl, isobutyl, tert-butyl, pentyl and hexyl. Suitable substituents include, for example, alkyl, hydroxy, halo-, alkoxy-, nitro-, COOH, $CO_2$-alkyl, alkenyl, CN, $NH_2$, $CF_3$ or a cyclic group. The skilled person will appreciate that the term "alkylene" is construed accordingly, i.e. in the context of the present invention, the term "alkylene" encompasses a straight or branched, substituted (mono- or poly-) or unsubstituted saturated carbon chain bearing a terminal Y group.

As used herein, the term "cycloalkyl" refers to a cyclic alkyl group which may be substituted (mono- or poly-) or unsubstituted. Suitable substituents include, for example, alkyl, hydroxy, halo-, alkoxy-, nitro-, COOH, $CO_2$-alkyl, alkenyl, CN, $NH_2$, $CF_3$ or a cyclic group.

As used herein, the term "alkenyl" refers to group containing one or more double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably still a $C_{2-10}$ alkenyl group, or preferably a $C_{2-6}$ alkenyl group. Suitable substituents include, for example, alkyl, hydroxy, halo-, alkoxy-, nitro-, COOH, $CO_2$-alkyl, alkenyl, CN, $NH_2$, $CF_3$ or a cyclic group. The skilled person will appreciate that the term "alkenylene" is construed accordingly, i.e. in the context of the present invention, the term "alkenylene" encompasses a straight or branched, substituted (mono- or poly-) or unsubstituted unsaturated carbon chain containing one or more double bonds and bearing a terminal Y group.

As used herein, the term "alkynyl" refers to a group containing one or more triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, or preferably a $C_{2-6}$ alkynyl group. Suitable substituents include, for example, alkyl, hydroxy, halo-, alkoxy-, nitro-, COOH, $CO_2$-alkyl, alkenyl, CN, $NH_2$, $CF_3$ or a cyclic group. The skilled person will appreciate that the term "alkynylene" is construed accordingly, i.e. in the context of the present invention, the term "alkynylene" encompasses a straight or branched, substituted (mono- or poly-) or unsubstituted unsaturated carbon chain containing one or more triple bonds and bearing a terminal Y group.

As used herein, the term "aryl" refers to a $C_{6-10}$ aromatic group which may be substituted (mono- or poly-) or unsubstituted. Typical examples include phenyl and naphthyl etc. Suitable substituents include, for example, alkyl, hydroxy, halo-, alkoxy-, nitro-, COOH, $CO_2$-alkyl, alkenyl, CN, $NH_2$, $CF_3$ or a cyclic group.

The term "heteroaryl" refers to an aryl group as defined above which contains one or more heteroatoms. Suitable heteroatoms will be apparent to those skilled in the art and include, for example, sulphur, nitrogen, oxygen, phosphorus and silicon. Suitable substituents include, for example, alkyl, hydroxy, halo-, alkoxy-, nitro-, COOH, $CO_2$-alkyl, alkenyl, CN, $NH_2$, $CF_3$ or a cyclic group.

The compounds of formula Ia (for use in the present invention) contain a polar functional group Y, which is attached to the aryl group, A, by means of a saturated or unsaturated hydrocarbyl linker group X. Suitable polar functional groups will be familiar to those skilled in the art and include, for example, any functional group which comprises one or more electronegative atoms, such as F, O, N, Cl or Br etc. Preferred polar functional groups include hydroxy, alkoxy, amine, imine, nitro, cyano, carbonyl-containing groups and sulfoxy-containing groups.

For compounds of formula Ia, especially preferred polar groups include $NO_2$, CN, $OR^3$, $COR^3$, $COOR^3$, $NR^3R^4$, $CONR^3R^4$, $SO_3H$, $SO_2R^3$, $SO_2NR^3R^4$ and $CF_3$, where each of $R^3$ and $R^4$ is independently H or a hydrocarbyl group.

For compounds of formula Ia, in one particularly preferred embodiment, Y is selected from $OR^3$, CN, $COOR^3$, $SO_2NR^3R^4$, $CONR^3R^4$, where each of $R^3$ and $R^4$ is independently H or a hydrocarbyl group.

For compounds of formula Ia, in an even more preferred embodiment of the invention, Y is selected from $OR^3$, CN, $COOR^3$, $CONR^3R^4$, where each of $R^3$ and $R^4$ is independently H or an alkyl group optionally substituted by one or more substituents selected from hydroxy, halo-, alkoxy-, nitro-, and a cyclic group.

For compounds of formula Ia, more preferably still, Y is selected from OH, CN, COOMe, COOH, $CONH_2$, CONHMe and $CONMe_2$.

For compounds of formula I, the polar group Y is selected from $NO_2$, OH, CN, $COR^3$, $COOR^3$, $NR^3R^4$, $CONR^3R^4$, SO$_3$H, SO$_2$—R$^3$, SO$_2$NR$^3$R$^4$ and CF$_3$, where each of R$^3$ and R$^4$ is independently H or a hydrocarbyl group.

For compounds of formula I, preferably polar group Y is selected from, OH, CN, COOR$^3$, SO$_2$NR$^3$R$^4$, CONR$^3$R$^4$, where each of R$^3$ and R$^4$ is independently H or a hydrocarbyl group.

For compounds of formula I, in an even more preferred embodiment of the invention, Y is selected from OH, CN, COOR$^3$, CONR$^3$R$^4$, where each of R$^3$ and R$^4$ is independently H or an alkyl group optionally substituted by one or more substituents selected from hydroxy, halo-, alkoxy-, nitro-, and a cyclic group.

For compounds of formula I, more preferably still, Y is selected from OH, CN, COOMe, COOH, CONH$_2$, CONHMe and CONMe$_2$.

For all the above embodiments, preferably each of R$^1$, R$^2$, R$^3$ and R$^4$ is independently H, an alkyl group, an aryl group, or a cycloalkyl group, each of which may be optionally substituted by one or more substituents selected from hydroxy, halo-, alkoxy-, nitro-, and a cyclic group.

In one particularly preferred embodiment of the invention, n is 0; i.e., B is absent and the —C(=O)Z moiety is attached directly to aryl group, A.

For compounds of formula I and Ia, preferably, X—Y is selected from

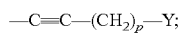

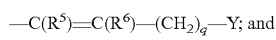

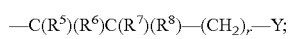

where each of R$^5$, R$^6$, R$^7$ and R$^8$ is independently H or alkyl, and each of p, q and r is independently 1 to 6, more preferably, 2, 3, or 4.

For compounds of formula I and Ia, even more preferably, X—Y is selected from

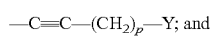

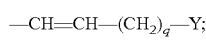

where each of p and q is independently 1 to 6, more preferably 2, 3, or 4.

In one preferred embodiment, R$^5$ and R$^6$ are both H.

For compounds of formula I and Ia, in one especially preferred embodiment, X—Y is

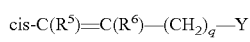

For compounds of formula I and Ia, in another preferred embodiment, X—Y is

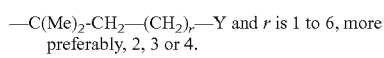

In another preferred embodiment, X—Y is (CH$_2$)$_s$—Y where s is 1 to 6, more preferably, 2, 3, 4 or 5.

Preferably, for compounds of formula I and Ia, A is an optionally substituted phenyl or pyridyl group, more preferably a phenyl group.

In another preferred embodiment, A is an unsubstituted phenyl or pyridyl group, more preferably an unsubstituted phenyl group.

In one particularly preferred embodiment, said compound is of formula Ib

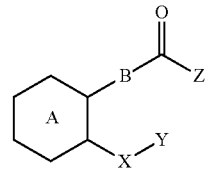

wherein A, B, X, Y and Z are as defined above.

In another particularly preferred embodiment, said compound is of formula Ic

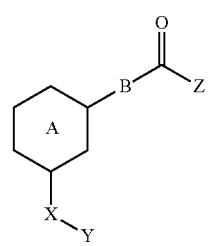

wherein A, B, X, Y and Z are as defined above.

Preferably, Z is OR$^1$ or NR$^1$R$^2$ and each of R$^1$ and R$^2$ is independently H, an alkyl or a cycloalkyl group, each of which may be optionally substituted by one or more OH or halogen groups.

In one preferred embodiment, Z is NR$^1$R$^2$ and each of R$^1$ and R$^2$ is independently H or an alkyl or a cycloalkyl group, each of which may be optionally substituted by one or more OH or halogen groups.

In one preferred embodiment, Z is OR$^1$ and R$^1$ is an alkyl or a cycloalkyl group, each of which may be optionally substituted by one or more OH or halogen groups.

In one preferred embodiment, Z is selected from OH, OEt, NHCH$_2$CH$_2$F, NH-cyclopropyl, NHCH(Me)CH$_2$OH and NHCH$_2$CH$_2$OH.

In a more preferred embodiment, Z is selected from OEt, NHCH$_2$CH$_2$F, NH-cyclopropyl, NHCH(Me)CH$_2$OH and NHCH$_2$CH$_2$OH.

The compounds of the invention were investigated for cannabinoid receptor binding and activation in vitro and for psychoactive potential in vivo, using mice. CNS levels were quantified using direct measurement of compound brain levels (for compounds lacking CNS effects). Peripheral cannabinoid activation was assessed using gut motility assays. Further details of the binding studies may be found in the accompanying Examples section.

Especially preferred compounds of the invention are selected from the following:
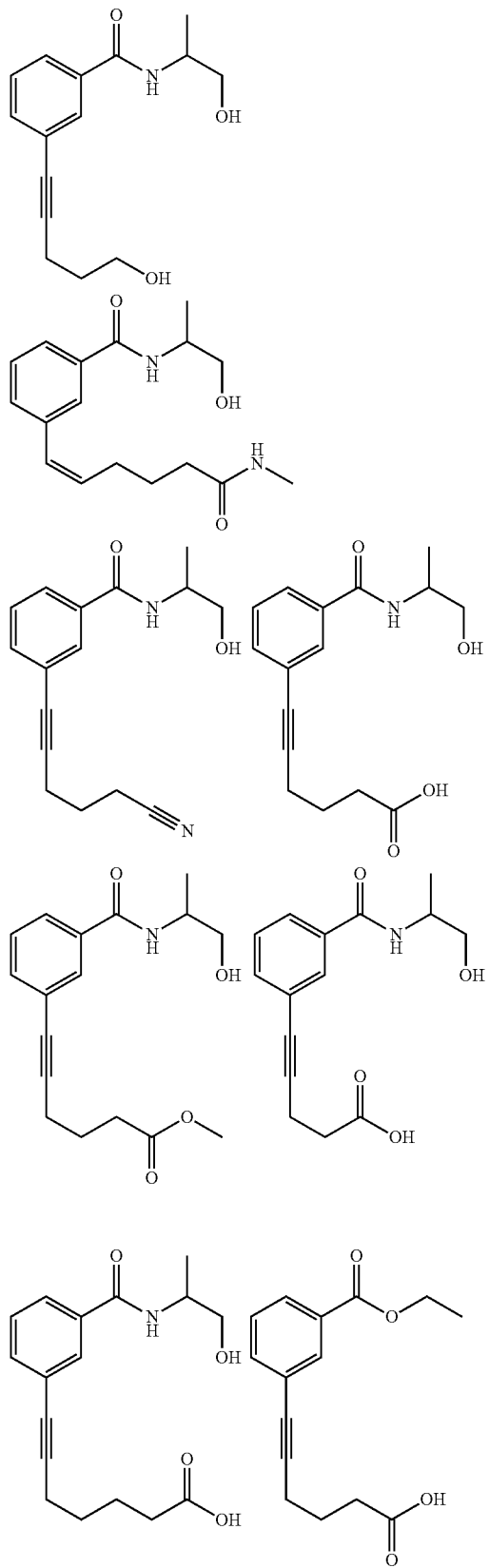
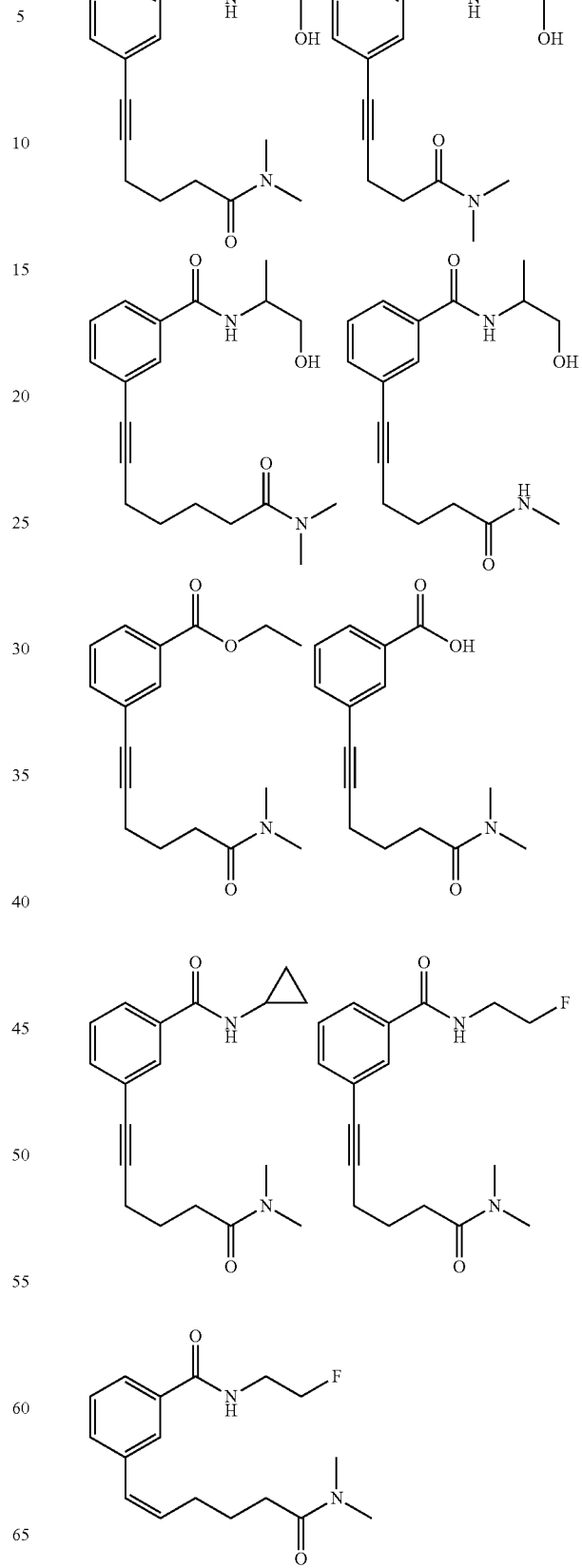

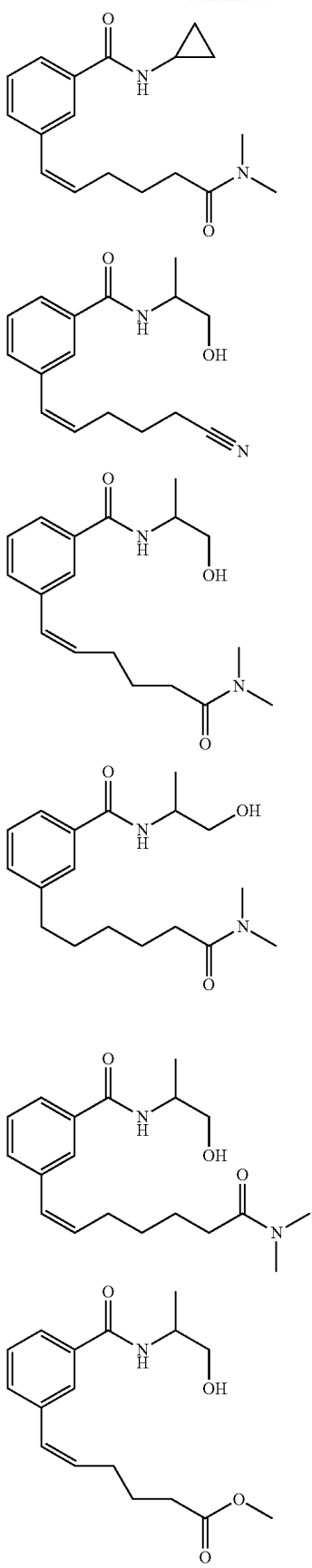

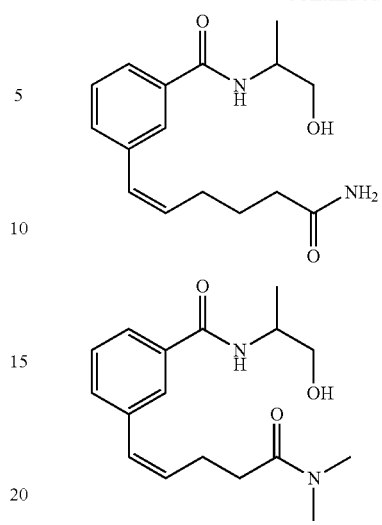

More preferably still, the compound of formula I is:

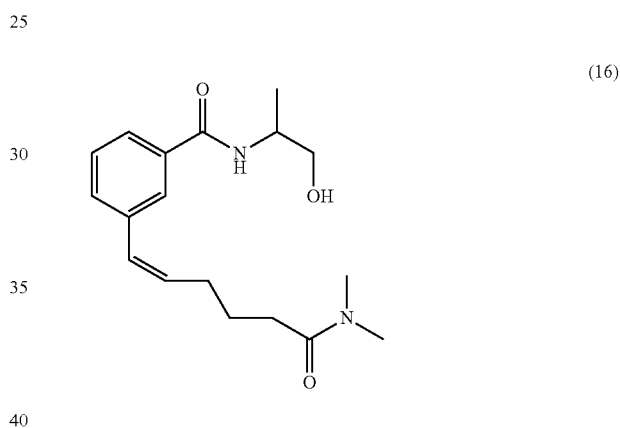

(16)

Advantageously, compound (16) was shown to modulate peripheral cannabinoid receptors without producing substantial CNS effects. Moreover, experiments carried out on CREAE mice suggest that compound (16) is capable of achieving selective inhibition of spasticity without producing CNS effects.

In an even more preferred embodiment, compound (16) is in the form of a racemic mixture.

Synthesis

Compounds of formula I and Ia are synthesised in accordance with Scheme 1 below.

Scheme 1

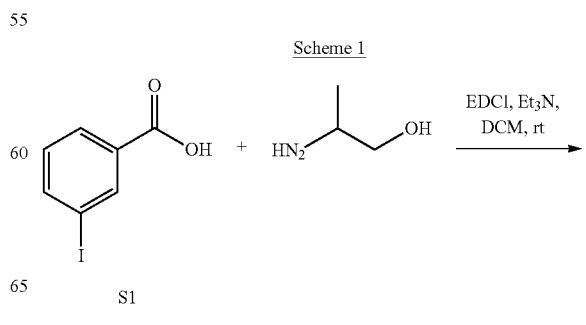

S1

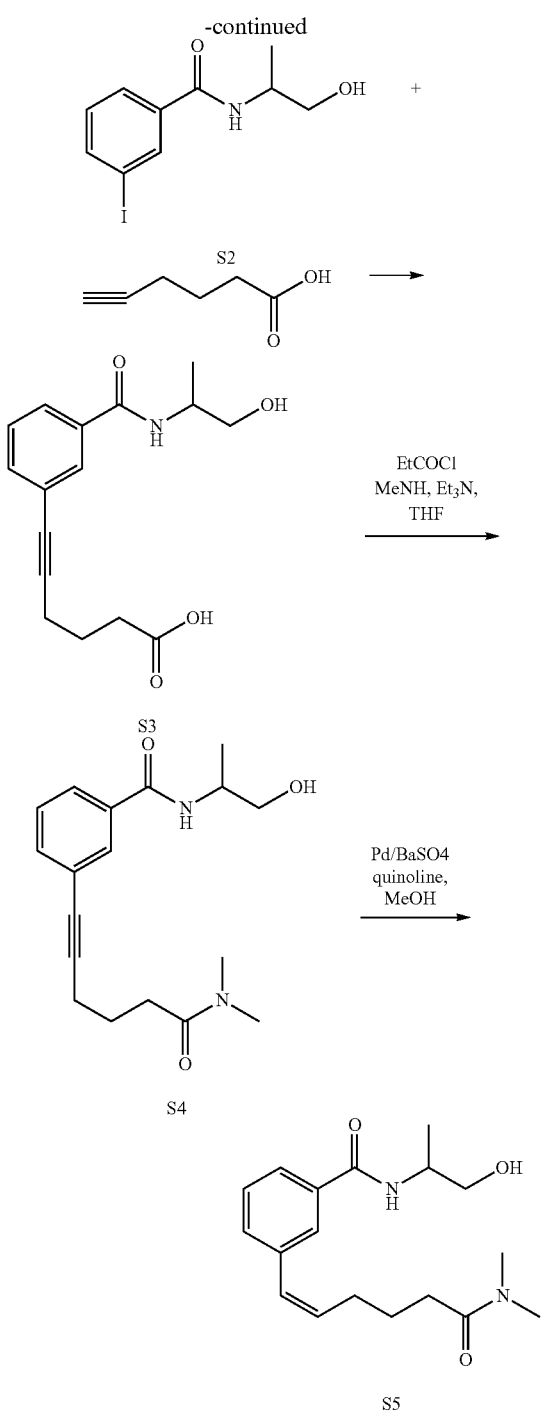

In brief, a palladium catalysed Songashira coupling reaction was used to insert a variety of alkyl side chains into 3-iodo methyl benzoate. The target compounds (S5) and related analogues were synthesised by a simple four-step route. First, the acid (S1) was reacted with DL alaninol in the presence of a diimide (EDCI) to give the amide (S2) in good yield. Palladium-catalysed coupling [Hoye, R. C. et al, *J. Org. Chem.* 1999, 64, 2450-2453; Hopper, A. T. et al, *J. Med. Chem.* 1998, 41, 420-427] of the amide with the alkyne acid in the presence of Cu$^I$I and pyrrolidine proceeded smoothly to give the alkyne (S3). The acid (S3) was quantitatively transformed into (S4) using ethylchloroformate and dimethylamine HCl. Lindlar catalysed reduction yielded the target alkene (S5). The flexibility of this method allows the synthesis of a large number of different compounds using a range of alkynes for the Sonogashira coupling, or by starting with a different amine for the amide formation in the first step.

Therapeutic Applications

Another aspect relates to the use of a compound of formula Ia according to the invention in the preparation of a medicament for treating a muscular disorder. Preferred embodiments are identical to those set forth above for compounds of general formula I.

Preferably, the muscular disorder is a neuromuscular disorder.

As used herein the phrase "preparation of a medicament" includes the use of a compound of formula I directly as the medicament in addition to its use in a screening programme for further agents or in any stage of the manufacture of such a medicament.

The term "muscular disorder" is used in a broad sense to cover any muscular disorder or disease, in particular a neurological disorder or disease, more particularly, a neurodegenerative disease or an adverse condition involving neuromuscular control. Thus, the term includes, for example, CREAE, MS, spasticity, Parkinson's disease, Huntingdon's Chorea, spinal cord injury, epilepsy, Tourettes' syndrome, and bladder spasm. Although there is no clear role for peripheral cannabinoid receptors in controlling spasticity in multiple sclerosis and EAE, the blood:CNS barriers are compromised in lesional areas and may provide selective access of therapeutic agents [Butter, C. et al, *J. Neurol. Sci.* 1991, 104, 9-12; Daniel, P. M. et al, *J. Neurol. Sci.* 1983, 60, 367-376; Juhler, M. et al, *Brain Res.* 1984, 302, 347-355].

In addition to the aforementioned disorders, the present invention also has applications in other fields where tremor or muscle spasm is present or is manifested, such as incontinence, asthma, brochial spasms, hic-coughs etc.

Another aspect relates to the use of a compound of formula Ia according to the invention in the preparation of a medicament for controlling spasticity and tremors.

The compounds of the invention also have therapeutic applications in the treatment of various gastrointestinal disorders.

Peripheral $CB_1$ receptors are known to modulate gastrointestinal motility, intestinal secretion and gastroprotection. The digestive tract contains endogenous cannabinoids (anandamide and 2-arachidonoylglycerol), and cannabinoid $CB_1$ receptors can be found on myenteric and submucosal nerves. Activation of prejunctionally/presynaptically-located enteric (intestinal) $CB_1$ receptors produces inhibition of electrically-induced contractions (an effect which is associated to inhibition of acetylcholine release from enteric nerves) in various isolated intestinal tissues, including the human ileum and colon. Cannabinoid agonists inhibit intestinal motility in rodents in vivo and this effect is mediated, at least in part, by activation of peripheral (i.e. intestinal) $CB_1$ receptors, both in the upper gastrointestinal transit [Izzo, A. A. et al, *Br. J. Pharmacol.* 2000, 129, 1627-1632; Landi, M. et al, *Eur. J. Pharmacol.* 2002, 450, 77-83] and in the colon [Pinto, L. et al, *Gastroenterology* 2002, 123, 227-234]. Thus, measurement of intestinal motility, in vivo is a useful model for evaluating the activity of peripheral-acting cannabinoid drugs.

Another aspect relates to the use of a compound of formula Ia according to the invention in the preparation of a medicament for treating a gastrointestinal disorder.

Preferably, the gastrointestinal disorder is selected from one or more of the following: gastric ulcers, Crohn's disease, secretory diarroehea and paralytic ileus.

As used herein the term "paralytic ileus" refers to paralysis or inactivity of the intestine that prohibits the passage of material within the intestine. Typically, this may be the result of anticholinergic drugs, injury or illness. Paralytic ileus is a common occurrence post surgically.

Preferably for all of the above therapeutic applications, the modulator selectively modulates peripheral cannabinoid receptors.

Even more preferably, the modulator selectively modulates peripheral cannabinoid receptors over central cannabinoid receptors.

As used herein, the term "selectively" refers to modulators that are selective for peripheral cannabinoid receptors. Preferably they are selective over central cannabinoid receptors. Preferably the modulators of the invention have a selectivity ratio for peripheral cannabinoid receptors of greater than 10 to 1, more preferably greater than 100 to 1, more preferably greater than 300 to 1, over central cannabinoid receptors. Selectivity ratios may readily be determined by the skilled person.

For some applications, preferably the modulator of the present invention has a $EC_{50}$ value of less than about 1000 nM, preferably less than 100 nM, more preferably less than about 75 nM, even more preferably less than about 50 nM, preferably less than about 25 nM, preferably less than about 20 nM, preferably less than about 15 nM, preferably less than about 10 nM, preferably less than about 5 nM.

More preferably, the modulator binds substantially exclusively to peripheral cannabinoid receptors.

In one particularly preferred embodiment, the modulator is a cannabinoid receptor agonist. As used herein the term "agonist" is used in its normal sense in the art, i.e., a chemical compound which functionally activates the receptor to which it binds.

In one particularly preferred embodiment, the modulator does not substantially agonise central cannabinoid receptors.

Even more preferably still, the modulator is substantially excluded from the CNS. Thus, the modulator is capable of modulating peripheral cannabinoid receptors without producing CNS effects, such as undesirable psychoactive effects.

Another aspect of the invention relates to a method of treating a disorder associated with the modulation of peripheral cannabinoid receptors, said method comprising administering to a subject in need thereof, a therapeutically effective amount of a compound of formula I as defined above.

Preferably, said disorder is associated with peripheral cannabinoid receptor deactivation.

Pharmaceutical Compositions

A further aspect of the invention relates to a pharmaceutical composition comprising a compound of the invention, or pharmaceutically acceptable salt thereof, as defined above admixed with a pharmaceutically acceptable diluent, excipient or carrier.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula I and Ia. The man skilled in the art will recognise compounds that possess an optical properties (one or more chiral carbon atoms) or tautomeric characteristics. The corresponding enantiomers and/or tautomers may be isolated/prepared by methods known in the art. Thus, the invention encompasses the enantiomers and/or tautomers in their isolated form, or mixtures thereof, such as for example, racemic mixtures of enantiomers.

Stereo and Geometric Isomers

Some of the specific agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of formula I and Ia wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, the one or more compounds of the invention are administered in combination with one or more other pharmaceutically active agents. In such cases, the compounds of the invention may be administered consecutively, simultaneously or sequentially with the one or more other pharmaceutically active agents.

Assay

The present invention uses—and also encompasses—an assay, wherein said assay is used to screen for agents that can modulate cannabinoid receptors, more preferably, peripheral cannabinoid receptors. Details of such assays are presented later.

Thus, another aspect of the invention relates to the use of a compound of formula Ia, or a pharmaceutically acceptable salt thereof, in an assay for identifying further compounds capable of modulating cannabinoid receptor activity. Preferably, the assay is a competitive binding assay.

In such an assay, one or more of appropriate targets—such as an amino acid sequence and/or nucleotide sequence—may be used for identifying an agent capable of modulating peripheral cannabinoid receptors. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesized on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO-A-84/03564.

It is expected that the assay methods of the present invention will be suitable for both small and large-scale screening of test compounds as well as in quantitative assays.

In a preferred aspect, the assay of the present invention utilises cells that display CB1 receptors on their surface. These cells may be isolated from a subject possessing such cells. However, preferably, the cells are prepared by transfecting cells so that upon transfection those cells display on their surface CB1 receptors.

One aspect of the invention relates to a process comprising the steps of:
(a) performing an assay method described hereinabove;
(b) identifying one or more candidate compounds capable of modulating one or more cannabinoid receptors; and
(c) preparing a quantity of said one or more candidate compounds.

Another aspect of the invention provides a process comprising the steps of:
(a) performing an assay method described hereinabove;
(b) identifying one or more candidate compounds capable of modulating one or more cannabinoid receptors;
(c) preparing a pharmaceutical composition comprising said one or more candidate compounds.

Another aspect of the invention provides a process comprising the steps of:
(a) performing an assay method described hereinabove;
(b) identifying one or more candidate compounds capable of modulating one or more cannabinoid receptors;
(c) modifying said one or more candidate compounds capable of modulating one or more cannabinoid receptors;
(d) performing the assay method described hereinabove;
(e) optionally preparing a pharmaceutical composition comprising said one or more candidate compounds.

The invention also relates to candidate compounds identified by the method described hereinabove.

Yet another aspect of the invention relates to a pharmaceutical composition comprising a candidate compound identified by the method described hereinabove.

Another aspect of the invention relates to the use of a candidate compound identified by the method described hereinabove in the preparation of a pharmaceutical composition for use in the treatment of muscular disorders and/or gastrointestinal disorders.

The above methods may be used to screen for a candidate compound useful as an modulators of one or more cannabinoid receptors, more preferably peripheral cannabinoid receptors.

Reporters

A wide variety of reporters may be used in the assay methods (as well as screens) of the present invention with preferred reporters providing conveniently detectable signals (eg. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al [1990, Serological Methods, A Laboratory Manual, APS Press, St Paul Minn.] and Maddox D E et al [1983, J Exp Med 15 8:121 1].

Examples of reporter molecules include but are not limited to (galactosidase, invertase, green fluorescent protein, luciferase, chloramphenicol, acetyltransferase, (glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

CB1 Receptor and CB2 Receptor Binding Assays

Details of a CB1 receptor binding assay and a CB2 receptor binding assay may be found in Petrocellis et al [2000 FEBS Letter 483 52-56]. The relevant information about those assays from that reference now follows. Other assays may be used.

Displacement assays for $CB_1$ receptors were carried out by using $^3$H]SR141716A (0.4 nM, 55 Ci/mmol, Amersham) as the high affinity ligand, and the filtration technique previously described [12-14], on membrane preparations (0.4 mg/tube) from frozen male CD rat brains (Charles River Italia) and in the presence of 100 µM PMSF. Specific binding was calculated with 1 µM SR 14176A (a gift from Sanofi Recherche, France) and was 84.0%. The spleen from CD rats were used to prepare membranes (0.4 mg/tube) to carry out $CB_2$ binding assays by using [$^3$H]WIN55, 212-2 (0.8$_n$M, 50.8 CI/mmol, NEN-Dupont) as described previously [14], and again in the presence of 100 µM PMSF. Specific binding was calculated with 1 µM HU-348 (a gift from Prof. R. Mechoulam and Pharmos) and was 75.0%. In all cases, $K_I$ values were calculated by applying the Cheng-prusoff equation to the $IC_{50}$ values (obtained by GraphPad) for the displacement of the bound radioligand by increasing concentrations of the test compounds. [Details on the specific references may be found in the document itself.]

Host Cells

Polynucleotides for use in the present invention—such as for use as modulators or for expressing modulators—may be introduced into host cells.

The term "host cell"—in relation to the present invention includes any cell that could comprise the modulator of the present invention.

Here, polynucleotides may be introduced into prokaryotic cells or eukaryotic cells, for example yeast, insect or mammalian cells.

Polynucleotides of the invention may introduced into suitable host cells using a variety of techniques known in the art, such as transfection, transformation and electroporation. For example, it is possible to cause transformation with recombinant viral vectors such as retroviruses, herpes simplex viruses and adenoviruses, direct injection of nucleic acids and biolistic transformation.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium E. coli is widely used as a host for heterologous gene expression. However, large amounts of heterologous protein tend to accumulate inside the cell. Subsequent purification of the desired protein from the bulk of E. coli intracellular proteins can sometimes be difficult.

In contrast to E. coli, bacteria from the genus Bacillus are very suitable as heterologous hosts because of their capability to secrete proteins into the culture medium. Other bacteria suitable as hosts are those from the genera Streptomyces and Pseudomonas.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as Aspergillus species (such as those described in EP-A-0184438 and EP-A-0284603) and Trichoderma species; bacteria such as Bacillus species (such as those described in EP-A-0134048 and EP-A-0253455), Streptomyces species and Pseudomonas species; and yeasts such as Kluyveromyces species (such as those described in EP-A-0096430 and EP-A-0301670) and Saccharomyces species. By way of example, typical expression hosts may be selected from Aspergillus niger, Aspergillus niger var. tubigenis, Aspergillus niger var. awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis and Saccharomyces cerevisiae.

Polypeptides that are extensively modified may require correct processing to complete their function. In those instances, mammalian cell expression systems (such as HEK-293, CHO, HeLA) are required, and the polypeptides are expressed either intracellularly, on the cell membranes, or secreted in the culture media if preceded by an appropriate leader sequence.

The use of suitable host cells—such as yeast, fungal, plant and mammalian host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include E. coli and Bacillus subtilis. Teachings on the transformation of prokaryotic hosts is well documented in the art, for example see Sambrook et al [Molecular Cloning: A Laboratory Manual, 2nd edition, 1989, Cold Spring Harbor Laboratory Press] and Ausubel et al, [Current Protocols in Molecular Biology (1995), John Wiley & Sons, Inc].

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al [1987, Yeast Biotechnology, D R Berry et al, eds, pp 401-429, Allen and Unwin, London] and by King et al [1989, Molecular and Cell Biology of Yeasts, E F Walton and G T Yarronton, eds, pp 107-133, Blackie, Glasgow].

For several reasons Saccharomyces cerevisiae is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny [1993, "Yeast as a vehicle for the expression of heterologous genes", Yeasts, Vol 5, Anthony H Rose and J Stuart Harrison, eds, 2nd edition, Academic Press Ltd.].

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al [1978, Proceedings of the National Academy of Sciences of the USA 75, 1929]; Beggs, J D [1978, Nature, London, 275, 104]; and Ito, H et al [1983, J Bacteriology 153, 163-168].

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus [Annu Rev Plant Physiol Plant Mol Biol [1991]42:205-225] and Christou [Agro-Food-Industry Hi-Tech March/April 1994 17-27]. Further teachings on plant transformation may be found in EP-A-0449375.

Further hosts suitable for the nucleotide sequence of the present invention include higher eukaryotic cells, such as insect cells or vertebrate cells, particularly mammalian cells, including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells.

The nucleotide sequence of the present invention may be stably incorporated into host cells or may be transiently expressed using methods known in the art. By way of example, stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the nucleotide sequence of the present invention. The precise amounts of the nucleotide sequence of the present invention may be empirically determined and optimised for a particular cell and assay.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins [Kroll D J et al (1993) DNA Cell Biol 12:441-53].

The present invention is further described by way of example, and with reference to the following figures wherein:

FIG. 1 shows rat vas deferens inhibition of contractions. In more detail, the $IC_{50}$ of compound (16) in this assay is approximately 0.1 nm. In the same assay R(+)WIN55,212 demonstrated an $IC_{50}$ at CB1 of approximately 5 nm, consistent with its known binding affinity. This assay demonstrates agonist potential and the effect of compound (16) was neutralised by the CB1-antagonist SR141716A.

Figure 2:
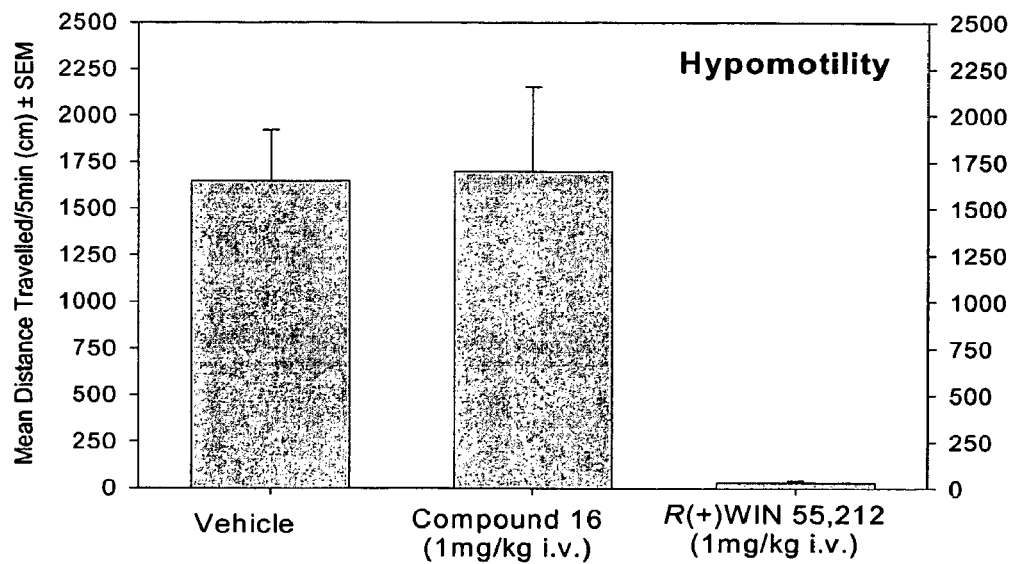

FIG. 2 shows hypomotiliy in wildtype mice.

Figure 3:
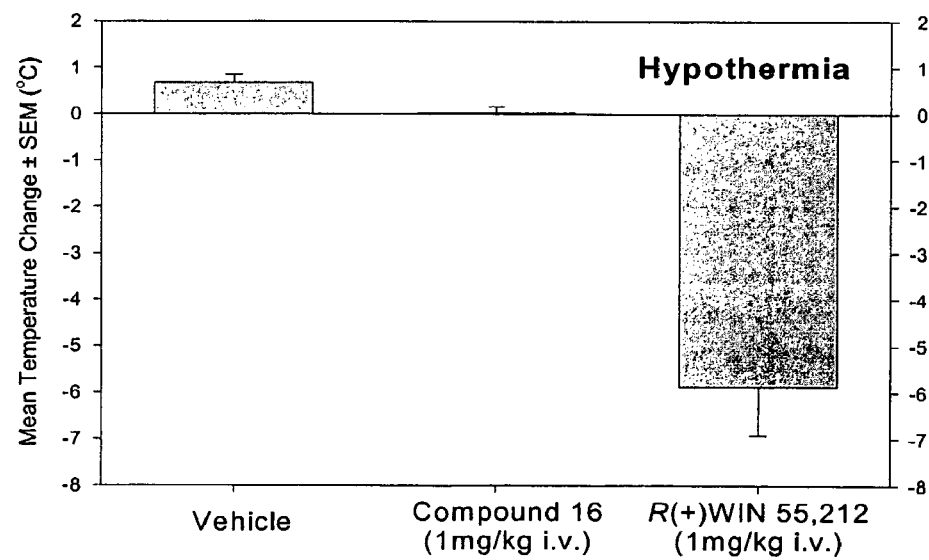

FIG. 3 shows hypothermia in wildtype mice. Temperature and 5 minute motility in a 27 cm$^2$ openfield in activity chamber was assessed [Brooks et al 2002] before and after (20 min) injection of vehicle (alchohol, cremophor, PBS (1:1:18), compound (16) or the CNS-penetrant CB1 agonist (R(+)Win 55,212. This latter compound induced typical cannabinmimetic effects whereas compound (16) was inactive at 1 mg/kg (above) and even at 20 mg/kg i.v.

Figure 4:
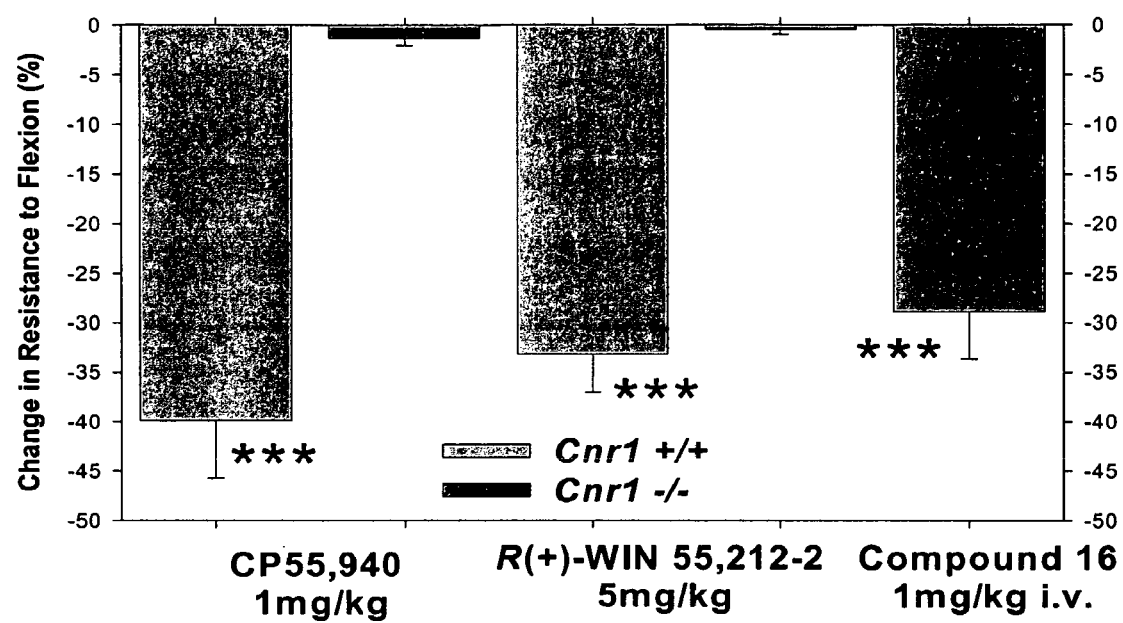

FIG. 4 shows the assessment of spasticity in CREAE mice. Spasticity developed following the development of chronic EAE induced by injection of mouse spinal cord homogenate in Freund's complete adjuvant on day 0 & 7. This occurred 60-80 days post-induction in wildtype ABH.Cnr1+/+ mice and 30-40 days post-induction in CB1 receptor gene (Cnr1)-deficient ABH.Cnr1−/− mice). Spasticity was assessed by resistance to full flexion of hindlimbs against a strain gauge [Baker et al 2000], before and after treatment with either the full $CB_1/CB_2$ agonist CP55,940 or full $CB_1/CB_2/$"$CB_3$" agonist injected intraperitoneally or compound (16) injected intravenously in vehicle (alcohol:cremophor:PBS (1:1:18)). The results represents the percentage change ±SEM from baseline (n<10-12 per group) 10 minutes after administration. Statistical analysis was performed on raw data and were analysed pairwise from baseline levels (*** P<0.001). The anti-spastic effects of CNS-penetrant agonists were lost in $CB_1$-deficient mice indicating that CB2/"CB3" is not a target for anti-spastic activity. Vehicle alone was inactive [Baker et al 2000]. Compound (16) exhibited significant anti-spastic activity in wildtype mice and was active when administered in PBS alone (not shown).

EXAMPLES

The compounds were purified by reverse-phase HPLC (Gilson) using preparative C-18 column (Hypersil PEP 100×

N-(2-hydroxy-1-methyl-ethyl)-3-iodobenzamide (1)

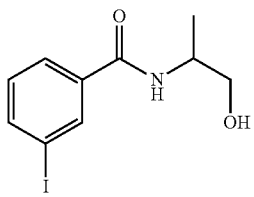

To a solution of 3-iodobenzoic acid (10.02 g, 40.30 mmol), in dry dichloromethane, at room temperature (180 mL) under a nitrogen atmosphere, EDCI (7.72 g, 40.30 mmol) was added followed by triethylamine (8.0 mL, 60.45 mmol) and the mixture was stirred at room temperature for further 5 minutes. DL Alaminol (3.02 g, 40.3 mmol) was then added and the mixture stirred at room temperature for 16 hrs. The reaction mixture was washed with a mixture of saturated brine and saturated sodium bicarbonate (1:1; 2×150 mL) followed by saturated brine solution (100 mL). The organics were separated and dried over magnesium sulfate and the solvent evaporated under vacuum. The residue was purified by flash column chromatography on silica gel (DCM:MeOH, 1% to 8% methanol gradient) to afford compound 1 (4.14 g, 13.6 mmol, 34% yield) as an off white solid.

$\delta(^1H)$ (CDCl$_3$); 1.41 (3H, d, J 6.8 Hz), 3.70 (1H, dd, J$_1$ 5.5, J$_2$ 10.9 Hz), 3.80 (1H, dd, J$_1$ 2.9, J$_2$ 10.9 Hz), 4.38 (1H, m), 6.46 (1H, m), 7.27 (2H, t, J 7.8 Hz), 7.93 (1H, d, J 7.88 Hz), 8.21 (1H, s).

$\delta(^{13}C)$ (CDCl$_3$); 17.49 (CH$_3$), 48.53 (CH$_2$), 67.19 (CH$_2$), 94.59 (C), 126.79 (CH), 129.58 (CH), 130.62 (CH), 136.37 (CH), 136.83 (C), 166.71 (C).

Calculated C$_{10}$H$_{11}$NO$_2$I.$_{1/2}$H$_2$O: C, 38.23%; H, 3.85%; N, 4.46%. found: C, 38.95%; H, 3.80%; N, 4.08% [*Drug Design and Discovery* 2000, 281-294].

General Procedure for Sonogashira Coupling Reaction

Method A

[*Tetrahedron* 2000, 56, 4777-4792] Bis(triphenylphosphine)palladium(II) chloride (3.5% mol), copper(I)iodide (8% mol) and triethylamine (4 mmol) were added to a solution of N-(2-hydroxy-1-methyl-ethyl)-3-iodobenzamide (1) (1 mmol) in DMF (5 mL). The mixture was stirred for 1 h under a nitrogen atmosphere at room temperature. The alkyne (1 mmol) was added and the reaction mixture was stirred at 60° C. for 2 hours. The reaction mixture was concentrated under vacuum and the residue was purified by short flash chromatography on silica gel (DCM:MeOH, 1% to 4% methanol gradient) to afford the desire compound.

N-(2-Hydroxy-1-methyl-ethyl)-3-(5-hydroxy-pent-1-ynyl)-benzamide (2)

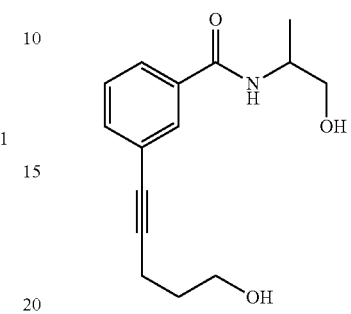

Method A was used to synthesise the named compound (2), coupling (1) (0.50 g, 1.64 mmol) with 4-pentyl-1-ol to yield N-(2-hydroxy-1-methyl-ethyl)-3-(5-hydroxy-pent-1-ynyl)-benzamide (2) (0.314 g, 1.20 mmol; 73%).

$\delta(^1H)$ (CDCl$_3$); 1.19 (3H, d, J 6.8 Hz), 1.68-1.81 (3H, m), 2.45 (2H, t, J 6.9 Hz), 3.04-3.17 (1H, m), 3.39-3.74 (5H, m), 4.12-4.23 (1H, m), 6.52 (1H, d, J 7.2 Hz), 7.22 (1H, dd, J$_1$ 6.3, J$_2$ 11.67 Hz), 7.39 (1H, d, J 7.7 Hz), 7.60 (1H, d, J 7.8 Hz), 7.68 (1H, s).

$\delta(^{13}C)$ (CDCl$_3$); 16.30 (CH$_3$), 17.440 (CH$_3$), 31.66 (CH$_2$), 48.49 (CH$_2$), 61.92 (CH$_2$), 67.00 (CH$_2$), 80.64 (C), 91.03 (C), 124.66 (C), 126.79 (CH), 128.93 (CH), 130.32 (CH), 134.74 (CH), 134.90 (C), 167.79 (C).

MS (ES) m/z 262 (M+H).

3-Hept-1-ynyl-N-(2-hydroxy-1-methyl-ethyl)-benzamide (3)

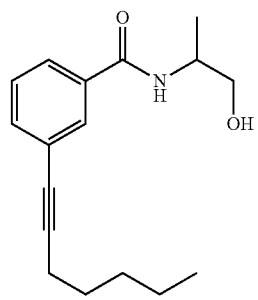

Method A was used to synthesise the named compound (3), coupling (1) (0.25 g, 0.84 mmol) with 1-heptyne to yield 3 (0.236 g, 0.80 mmol; 95%) as a colourless oil.

$\delta(^1H)$ (CDCl$_3$); 0.89 (3H, t, J 6.8 Hz), 1.22 (3H, d, J 6.8 Hz), 1.29-1.41 (4H, m), 1.53-1.60 (2H, m), 2.36 (2H, t, J 7.1 Hz), 2.81 (2H, m), 2.89 (1H, m), 4.15-4.19 (1H, m), 6.67 (1H, d, J 7.3 Hz), 7.24 (1H, t, J 7.7 Hz), 7.44 (1H, d, J 7.7 Hz), 7.63 (1H, d, J 7.8 Hz), 7.73 (1H, s).

$\delta(^{13}C)$ (CDCl$_3$); 14.31 (CH$_3$), 17.40 (CH$_3$), 19.71 (CH$_2$), 22.57 (CH$_2$), 28.73 (CH$_2$), 31.49 (CH$_2$), 48.44 (CH), 66.79 (CH$_2$), 67.00 (CH$_2$), 80.13 (C), 92.04 (C), 124.97 (C), 126.53 (CH), 128.90 (CH), 130.33 (CH), 132.45 (CH), 134.95 (C), 167.80 (C).

MS (ES) m/z 274 (M+H).

3-(5-Cyano-pentil-1-ynyl)-N-(2-hydroxy-1-methyl-ethyl)benzamide (7)

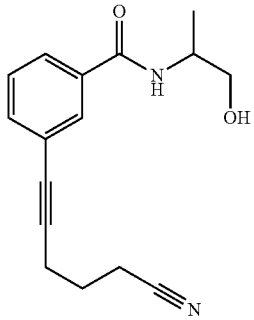

7

Method A was used to synthesise the named compound (7), coupling (1) (0.300 g, 0.983 mmol) with hex-5-ynenitrile (119 mg, 1.28 mmol) to give 0.124 g of 3-(5-cyano-pentil-1-ynyl)-N-(2-hydroxy-1-methyl-ethyl)benzamide (7) in 46.6% yield after purification.

$\delta(^1H)$ (CDCl$_3$); 1.29 (3H, d, J 6.8 Hz), 1.97 (2H, m), 2.55-2.64 (4H, m), 3.67 (1H, m), 3.78 (1H, m), 4.28 (1H, m), 6.41 (1H, m), 7.36 (1H, t, J 7.8 Hz), 7.51 (1H, d, J 7.8 Hz), 7.72 (1H, d, J 7.8 Hz), 7.80 (1H, s).

$\delta(^{13}C)$ (CDCl$_3$); 16.68 (CH$_2$), 17.50 (CH$_3$), 18.94 (CH$_2$), 24.87 (CH$_2$), 48.52 (CH), 67.22 (CH$_2$), 81.95 (C), 88.5 (C), 119.55 (C), 124.13 (C), 127.07 (CH), 129.06 (CH), 130.45 (CH), 134.80 (CH), 135.00 (C), 167.61 (C).

MS (ES) m/z 271 (M+H).

Method B

[*J. Org. Chem.* 1999, 64, 4777-4792; *J. Med. Chem.* 1998, 41, 420-427] Tetrakis(triphenylphosphine)palladium(0) (2% mol) and copper(I) iodide (7% mol) were added to pyrrolidine (15 mL) in a round-bottomed flask and stirred at room temperature under a nitrogen atmosphere, for 5 minutes. To this solution N-(2-hydroxy-1-methyl-ethyl)-3-iodobenzamide (1 mmol) was added and stirred for an additional 15 minutes at room temperature. The alkyne (1 mmol) was added and the reaction mixture was stirred at 60° C. for 3 hours. The reaction mixture was concentrated under vacuum, the residue was treated with DOWEX50 WX80 (10× weight of the starting material); DOWEX50 WX80 was washed with acetonitrile (3×20 mL), then suspended in a mixture of acetonitrile/water (3/1). The residue above was dissolved in acetonitrile/water (1:1, 20 mL), and was added to the resin suspension and shaken for 20 minutes. The resin was filtered off, washed with acetonitrile/water (3/1) and the solvent removed from the filtrate under vacuum. The residue purified by short flash column chromatography on silica gel (DCM:MeOH:AcOH, 1% to 8% methanol gradient, with 1% AcOH) to yield the desired compound.

Method B$^1$: The treatment of the crude material with DOWEX50 WX80 was performed in the presence of methanol instead of acetonitrile/water (3/1).

6-[3-(2-Hydroxy-1-methyl-ethylcarbamoyl)phenyl]-hex-5-ynoic acid (4)

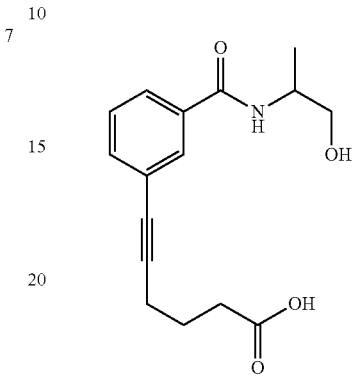

4

The iodobenzamide (1) (2.00 g, 6.5 mmol) was coupled with 5-hexynoic acid using method B giving product (4) (1.87 g, 6.42 mmol; 99% yield).

$\delta(^1H)$(CDCl$_3$); 1.49 (3H, d, J 6.8 Hz), 2.14 (2H, t, J 7.2 Hz), 2.67-2.76 (4H, m), 3.83-3.90 (2H, m) 4.39-4.45 (1H, m) 7.64 (1H, t, J 7.7 Hz), 7.76 (1H, d, J 7.7 Hz), 7.99 (1H, d, J 7.8 Hz), 8.10 (1H, s).

$\delta(^{13}C)$ (CD$_3$OD); 17.47 (CH$_2$), 19.99 (CH$_3$), 36.25 (CH$_2$), 66.54 (CH$_2$), 81.82 (C), 91.53 (C), 126.03 (C), 128.05 (CH), 129.99 (CH), 131.75 (CH), 135.69 (CH), 136.58 (C), 168.538 (C).

MS (CI) m/z 290 (M+H).

6-[3-(2-Hydroxy-1-methyl-ethylcarbamoyl)-phenyl]-hex-5-ynoic acid methyl ester (20)

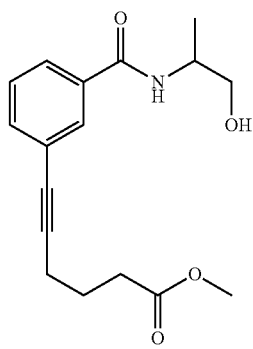

20

If the method B$^1$ was used in the work up, 6-[3-9(2-Hydroxy-1-methyl-ethylcarbamoyl)-phenyl]-hex-5-ynoic acid methyl ester (20) was obtained instead of the acid 4. 1 (0.100 g, 0.32 mmol) was coupled with 5-hexynoic acid (0.091 g, 0.276 mmol) to give 20 (0.091 g, 0.27 mmol, 85% yield).

$\delta(^1H)$ (CDCl$_3$); 1.31 (3H, d, J 6.8 Hz), 1.96 (2H, t, J 7.2 Hz), 2.03 (3H, s), 2.39-2.59 (4H, m), 3.61-3.72 (2H, m), 4.19-4.27 (1H, m), 7.46 (1H, t, J 7.7 Hz), 7.48 (1H, d, J 7.6 Hz), 7.94 (1H, d, J 7.8 Hz), 8.05 (1H, s).

5-[3-(2-Hydroxy-1-methyl-ethylcarbamoyl)phenyl]-hex-4-ynoic acid (5)

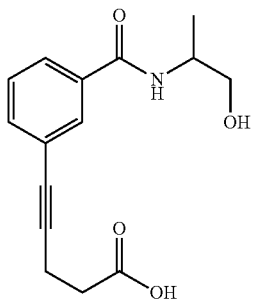

5

The iodobenzamide (1) (2.00 g, 6.5 mmol) was coupled with 5-hexynoic acid using method B yielding (4) (1.87 g, 6.42 mmol; 99% yield).

δ($^1$H) (CD$_3$OD); 1.40 (3H, d, J 6.8 Hz), 2.70-2.824 (2H, m), 2.87-2.89 (2H, m), 3.74-3.77 (2H, m), 4.30-4.36 (1H, m), 7.54 (1H, t, J 7.7 Hz), 7.6 (1H, d, J 7.6 Hz), 7.91 (1H, d, J 7.8 Hz), 7.99 (1H, s).

δ($^{13}$C) (CD$_3$OD); 16.21 (CH$_2$), 17.03 (CH$_3$), 34.94 (CH$_2$), 66.08 (CH$_2$), 81.05 (C), 90.53 (C), 125.46 (C), 127.70 (CH), 129.56 (CH), 131.39 (CH), 135.27 (CH), 136.19 (C), 169.28 (C), 175.80 (C).

7-[3-(2-Hydroxy-1-methyl-ethylcarbamoyl)phenyl]-hex-6-ynoic acid (6)

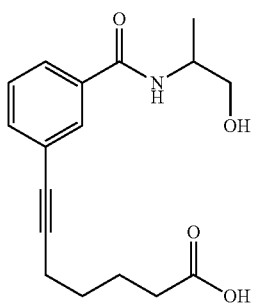

6

The iodobenzamide (1) (0.50 g, 1.64 mmol) was coupled with 6-heptynoic acid (0.212 g, 1.64 mmol) using method B to give 7-[3-(2-hydroxy-1-methyl-ethylcarbamoyl)phenyl]-hex-6-ynoic acid (6) (0.487 g, 1.60 mmol; 98% yield).

δ($^1$H) (CD$_3$OD); 1.22 (3H, d, J 6.8 Hz), 1.44-1.68 (2H, m), 1.73-1.80 (2H, m), 2.30-2.46 (2H, m), 3.54-3.63 (2H, m), 4.12-4.39 (1H, m) 7.36 (1H, t, J 7.7 Hz), 7.49 (1H, d, J 7.7 Hz), 7.72 (1H, d, J 7.8 Hz), 7.82 (1H, s).

δ($^{13}$C) (CD$_3$OD); 17.06 (CH$_3$), 19.70 (CH$_2$), 25.39 (CH$_2$), 29.23 (CH$_2$), 49.16 (CH$_2$), 66.14 (CH$_2$), 81.16 (C), 91.55 (C), 125.75 (C), 127.53 (CH), 129.54 (CH), 131.32 (CH), 135.24 (CH), 136.20 (C), 169.34 (C).

3-(5-Carboxy-pent-1-ynyl)-benzoic acid ethyl ester (14)

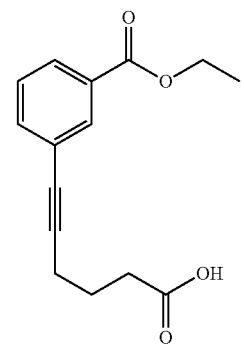

14

The iodobenzamide (1) (1.50 g, 5.4 mmol) was coupled with 5-hexynoic acid using method B to give 3-(5-carboxy-pent-1-ynyl)-benzoic acid ethyl ester (14) (0.903 g, 3.4 mmol; 64% yield).

δ($^1$H) (CDCl$_3$); 1.39 (3H, d, J 7.1 Hz), 1.83-1.99 (2H, m), 2.44-2.59 (4H, m), 4.37 (2H, q, J 7.1 Hz), 7.35 (1H, t, J 7.8 Hz), 7.58 (1H, d, J 7.6 Hz), 7.82 (1H, d, J 7.8 Hz), 7.92 (1H, s).

δ($^{13}$C) (CDCl$_3$); 14.28 (CH$_3$), 18.79 (CH$_2$), 23.59 (CH$_2$), 61.13 (CH$_2$), 80.72 (C), 89.67 (C), 124.07 (C), 128.28 (CH), 128.72 (CH), 130.69 (C), 132.22 (CH), 135.65 (CH), 166.03 (C).

Synthesis of Amides

Method C:

To a solution of the alkynoic acid (1 mmol) in dry THF (6 mL) under nitrogen atmosphere, triethylamine (2 mmol) was added and then cooled at −10° C. To the reaction mixture ethyol chloroformate (1 mmol) was added and then stirred for further minutes at −10° C. In the meantime a solution of amine hydrochloride (3 mmol), water (0.88 mL), triethylamine (0.63 mL, 6 mmol) and THF (1.76 mL) was prepared and added dropwise to the reaction mixture. The reaction was left warming up to 5° C. in 1.5 h and then stirred at room temperature for a further 30 minutes. The mixture was poured into a 1:1 mixture of saturated brine and saturated sodium bicarbonate (50 mL) and then extracted with DCM (5×50 mL). The organic layer was evaporated under vacuum, the residue was purified by short column chromatography on silica gel (DCM:MeOH, 1% to 10% methanol gradient) to give the desired compound.

3-(5-Dimethylcarbamoyl-pent-1-ynyl)-N-(2-hydroxy-1-methyl-ethyl)benzamide (8)

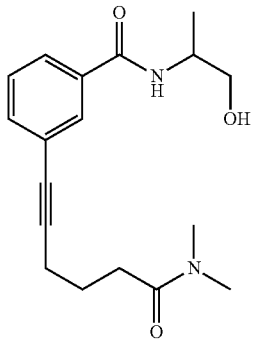

8

6-[3-(2-Hydroxy-1-methyl-ethylcarbamoyl)phenyl]-hex-5-ynoic acid (4) (0.109 g, 0.377 mmol) was reacted using method C with dimethylamine hydrochloride to obtain 8 (0.115 g, 0.363 mmol; 96% yield).

$\delta(^1H)$ (CDCl$_3$); 1.29 (3H, d, J 6.8 Hz), 1.81-1.94 (2H, m), 2.37-2.47 (4H, m), 2.91 (3H, s), 3.00 (3H, s), 3.38-3.64 (2H, m) 4.19-4.43 (1H, m) 6.78 (1H, d, J 7.2 Hz), 7.29 (1H, t, J 7.7 Hz), 7.42 (1H, d, J 7.7 Hz), 7.68 (1H, d, J 7.8 Hz), 7.75 (1H, s).

$\delta(^{13}C)$ (CDCl$_3$); 17.42 (CH$_3$), 19.36 (CH$_2$), 24.45 (CH$_2$), 32.30 (CH$_2$), 35.83 (CH$_3$), 37.67 (CH$_3$), 48.51 (CH), 66.90 (CH$_2$), 80.91 (C), 90.92 (C), 124.60 (C), 126.85 (CH), 128.85 (CH), 130.39 (CH), 134.58 (CH), 135.13 (C), 167.63 (C), 172.87 (C).

MS (ES) m/z 317 (M+H).

3-(4-Dimethylcarbamoyl-pent-1-ynyl)-N-(2-hydroxy-1-methyl-ethyl)benzamide (9)

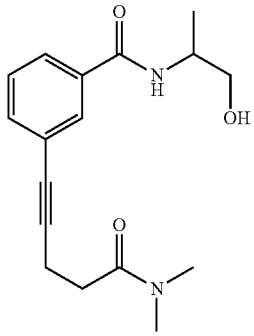

9

5-[3-(2-Hydroxy-1-methyl-ethylcarbamoyl)phenyl]-hex-4-ynoic acid (5) (0.100 g, 0.36 mmol) was reacted using method C with dimethylamine hydrochloride to obtain 9 (0.084 g, 0.28 mmol; 77% yield).

$\delta(^1H)$ (CDCl$_3$); 1.26 (3H, d, J 6.8 Hz), 2.58-2.75 (4H, m), 2.91 (3H, s), 3.01 (3H, s), 3.40-3.77 (2H, m), 4.19-4.43 (1H, m), 6.72 (1H, d, J 7.1 Hz), 7.29 (1H, t, J 7.8 Hz), 7.44 (1H, d, J 7.7 Hz), 7.67 (1H, d, J 7.8 Hz), 7.96 (1H, s).

$\delta(^{13}C)$ (CDCl$_3$); 15.39 (CH$_2$), 16.98 (CH$_3$), 32.43 (CH$_2$), 35.49 (CH$_3$), 37.15 (CH$_3$), 48.13 (CH), 66.64 (CH$_2$), 80.14 (C), 90.19 (C), 123.99 (C), 126.60 (CH), 128.43 (CH), 129.95 (CH), 134.19 (CH), 134.75 (C), 167.26 (C), 171.14 (C).

3-(6-Dimethylcarbamoyl-pent-1 ynyl)-N-(2-hydroxy-1-methyl-ethyl)benzamide (10)

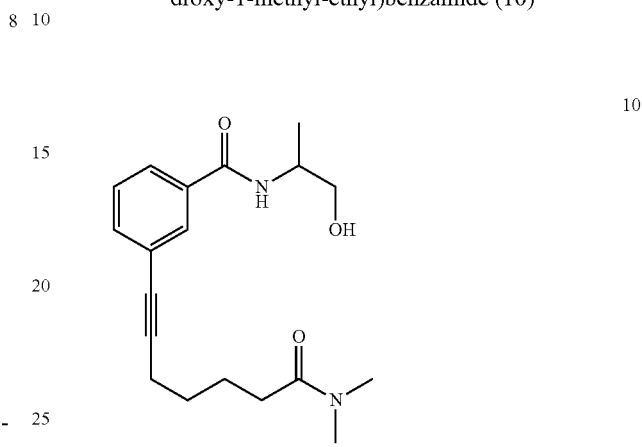

10

7-[3-(2-Hydroxy-1-methyl-ethylcarbamoyl)phenyl]-hex-6-ynoic acid (6) (0.100 g, 0.32 mmol) was reacted using method C with dimethylamine hydrochloride to obtain 10 (0.091 g, 0.276 mmol; 85% yield).

$\delta(^1H)$ (CDCl$_3$); 1.26 (3H, d, J 6.8 Hz), 1.59-1.80 (4H, m), 2.31-2.43 (4H, m), 2.91 (3H, s), 2.98 (3H, s), 3.60 (1H, dd, J$_1$ 11.1 Hz, J$_{2_1}$ 5.3 Hz), 3.74 (1H, dd, J$_1$ 11.1 Hz, J$_{2_1}$ 3.5 Hz), 6.85 (1H, d, J 7.2 Hz), 7.27 (1H, t, J 7.7 Hz), 7.43 (1H, d, J 7.7 Hz), 7.69 (1H, d, J 7.8 Hz), 7.76 (1H, s).

$\delta(^{13}C)$ (CDCl$_3$); 16.99 (CH$_3$), 19.15 (CH$_2$), 24.30 (CH$_2$), 28.19 (CH$_2$), 32.45 (CH$_2$), 35.46 (CH$_3$), 37.33 (CH$_3$), 48.12 (CH), 66.50 (CH$_2$), 80.37 (C), 90.85 (C), 124.26 (C), 126.55 (CH), 128.44 (CH), 129.98 (CH), 134.06 (CH), 134.74 (C), 167.24 (C), 172.98 (C).

3-(5-Methylcarbamoyl-pent-1-ynyl)-N-(2-hydroxy-1-methyl-ethyl)benzamide (22)

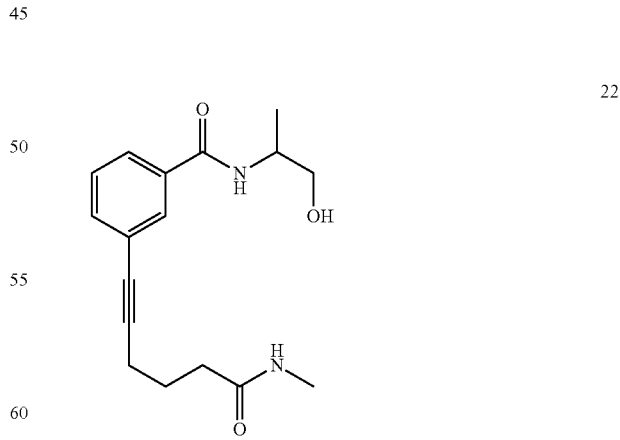

22

6-[3-(2-Hydroxy-1-methyl-ethylcarbamoyl)phenyl]-hex-5-ynoic acid (4) (0.400 g, 1.37 mmol) was reacted using method C with methylamine hydrochloride (0.609 g) to give 3-(5-methylcarbamoyl-pent-1-ynyl)-N-(2-hydroxy-1-methyl-ethyl)benzamide (22) (0.221 g, 0.724 mmol; 53% yield).

δ($^1$H) (CDCl$_3$); 1.29 (3H, d, J 6.8 Hz), 1.88-1.97 (2H, m), 2.33-2.44 (4H, m), 2.79 (3H, s), 2.81 (3H, s), 3.65 (2H, dd, J$_1$ 5.6, J$_2$ 11.1 Hz), 3.79 (2H, dd, J$_1$ 3.6, J$_2$ 11.1 Hz), 4.23-4.31 (1H, m), 5.93 (1H, bs), 6.55 (1H, d, J 7.3 Hz), 7.33 (1H, t, J 7.7 Hz), 7.7 (1H, d, J 7.7 Hz), 7.69 (1H, d, J 7.7 Hz), 7.77 (1H, s).

δ($^{13}$C) (CDCl$_3$); 17.44 (CH$_3$), 19.29 (CH$_2$), 26.70 (CH$_3$), 35.58 (CH$_2$), 48.57 (CH), 67.20 (CH$_2$), 80.91 (C), 90.69 (C), 124.60 (C), 126.81 (CH), 128.95 (CH), 130.41 (CH), 134.68 (CH), 134.98 (C), 167.63 (C), 173.47 (C).

3-(5-Dimethylcarbamoyl-pent-ynyl)benzoic acid ethyl ester (23)

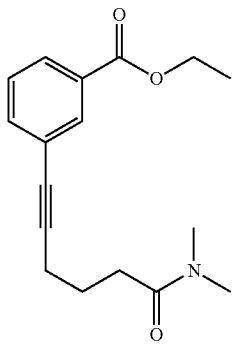

3-(5-Carboxy-pent-1-ynyl)-benzoic acid ethyl ester (4) (0.900 g, 3.4 mmol) was reacted using method C with dimethylamine hydrochloride to give 3-(5-dimethylcarbamoyl-pent-ynyl)benzoic acid ethyl ester (23) (0.873 g, 3.04 mmol; 89% yield).

δ($^1$H) (CDCl$_3$); 1.39 (3H, d, J 7.1 Hz), 1.87-2.00 (2H, m), 2.43-2.54 (4H, m), 2.95 (3H, s), 3.03 (3H, s), 4.37 (2H, q, J 7.1 Hz), 7.32 (1H, t, J 7.8 Hz), 7.55 (1H, d, J 7.6 Hz), 7.92 (1H, d, J 7.8 Hz), 8.04 (1H, s).

δ($^{13}$C) (CDCl$_3$); 14.28 (CH$_3$), 18.97 (CH$_2$), 24.01 (CH$_2$), 31.87 (CH$_2$), 35.39 (CH$_3$), 37.20 (CH$_3$), 61.10 (CH$_2$), 80.39 (C), 90.60 (C), 124.26 (C), 128.27 (CH), 128.60 (CH), 130.69 (C), 132.62 (CH), 135.58 (CH), 166.0 (C), 172.26 (C).

3-(5-Dimethylcarbamoyl-pent-1-ynyl)-benzoic acid (24)

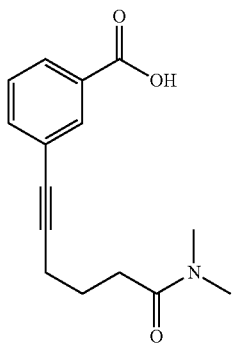

3-(5-Dimethylcarbamoyl-pent-ynyl)benzoic acid ethyl ester (0.800 g, 2.78 mmol) was treated with sodium hydroxide 1M solution (6 mL) overnight. To the reaction mixture 7 mL of HCl 1M solution was added and the solvent was removed under vacuum. The residue was triturated with ethyl acetate, to give 3-(5-dimethylcarbamoyl-pent-1-ynyl)-benzoic acid (24) (0.590 g, 2.05 mmol; yield 74%) as white off powder.

δ($^1$H) (CDCl$_3$); 1.85-2.00 (2H, m), 2.48-2.58 (4H, m), 2.93 (3H, s), 3.08 (3H, s), 7.40 (1H, t, J 7.8 Hz), 7.58 (1H, d, J 7.6 Hz), 7.91 (1H, d, J 7.8 Hz), 7.97 (1H, s).

N-Cyclopropyl-3-(5-dimethylcarbamoyl-pent-1-ynyl)benzamide (25)

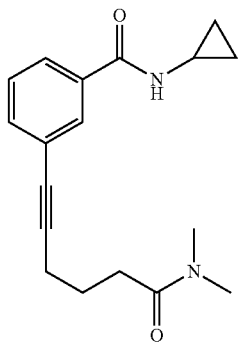

To a solution of 3-(5-dimethylcarbamoyl-pent-1-ynyl)-benzoic acid (0.100 g, 0.38 mmol) in dry dichloromethane (1.5 mL) under a nitrogen atmosphere at room temperature, EDCI (0.0728 g, 0.38 mmol) was added followed by triethylamine (0.162 mL, 1.14 mmol), the resulting mixture was stirred at room temperature for further minutes. Cyclopropylamine (0.027 g, 0.38 mmol) was then added and the mixture stirred at room temperature for 16 hrs. The reaction mixture was washed with a mixture of saturated brine and saturated sodium bicarbonate (1:1; 2×150 mL) followed by saturated brine solution (100 mL). The organic layer was separated and dried over magnesium sulfate and the solvent evaporated under vacuum. The residue was purified by flash column chromatography on silica gel (DCM:MeOH, 95% to 5% methanol gradient) to afford N-cyclopropyl-3-(5-dimethylcarbamoyl-pent-1-ynyl)benzamide (25) (0.10 g, 0.34 mmol, 91% yield).

δ($^1$H) (CDCl$_3$); 0.59-0.64 (2H, m), 0.83-0.90 (2H, m), 1.90-2.00 (2H, m), 2.49-2.53 (4H, m), 2.87-2.93 (1H, m), 2.95 (3H, s), 3.03 (3H, s), 6.25 (1H, bs), 7.33 (1H, t, J 7.8 Hz), 7.44-7.49 (1H, m), 7.63-7.72 (1H, m), 7.84 (1H, s).

δ($^{13}$C) (CDCl$_3$); 6.76 (CH$_2$), 18.98 (CH$_2$), 23.16 (CH), 24.02 (CH$_2$), 31.87 (CH$_2$), 35.39 (CH$_3$), 37.22 (CH$_3$), 80.39

3-(5-dimethylcarbamoyl-pent-1-ynyl)-N-(2-fluoro-ethyl)benzamide (26)

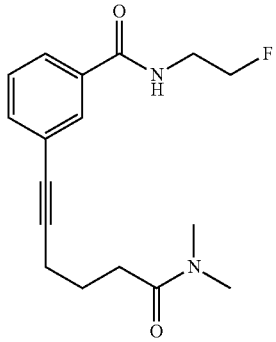

26

To a solution of 3-(5-dimethylcarbamoyl-pent-1-ynyl)-benzoic acid (0.100 g, 0.38 mmol) in dry dichloromethane (1.5 mL) under a nitrogen atmosphere at room temperature, EDCI (0.0728 g, 0.38 mmol) was added followed by triethylamine (0.162 mL, 1.14 mmol), the resulting mixture was stirred at room temperature for further minutes. 2-Fluoro ethylamine (0.189 g, 1.9 mmol) was then added and the mixture stirred at room temperature for 16 hrs. The reaction mixture was washed with a mixture of saturated brine and saturated sodium bicarbonate (1:1; 2×150 mL) followed by saturated brine solution (100 mL). The organic layer was separated and dried over magnesium sulfate and the solvent evaporated under vacuum. The residue was purified by flash column chromatography on silica gel (DCM:MeOH, 95% to 5% methanol gradient) to afford 3-(5-dimethylcarbamoyl-pent-1-ynyl)-N-(2-fluoro-ethyl)benzamide (26) (0.103 g, 0.34 mmol, 91% yield).

$\delta(^{1}H)$ (CDCl$_3$); 1.83-2.00 (2H, m), 2.48-2.52 (4H, m), 2.94 (3H, s), 3.02 (3H, s), 3.68-3.72 (1H, m), 3.73-3.82 (1H, m), 4.50 (3H, t, J 4.8 Hz), 4.66 (3H, t, J 4.8 Hz), 6.69 (1H, bs), 7.34 (1H, t, J 7.7 Hz), 7.44-7.46 (1H, m), 7.62-7.68 (1H, m), 7.93 (1H, s).

$\delta(^{13}C)$ (CDCl$_3$); 18.97 (CH$_2$), 24.01 (CH$_2$), 31.87 (CH$_2$), 35.40 (CH$_3$), 37.23 (CH$_3$), 40.35 (CH$_2$), 40.62 (CH$_2$), 80.37 (C), 81.57 (CH$_2$), 81.57 (CH$_2$), 90.75 (C), 124.48 (C), 126.24 (CH), 128.40 (CH), 130.05 (CH), 131.94 (CH$_2$), 134.45 (C), 167.04 (C), 172.30 (C).

General Method for Lindlar Hydrogenation
Method D:

Quinoline (143 µL, 1.3 mmol), palladium on barium sulphate reduced (5%) (143 mg) and the alkyne (1 mmol) were combined in methanol (14 mL) and stirred under atmospheric pressure of hydrogen until the $^{1}$HNMR of the crude showed that the reduction was complete. The catalyst was removed by filtration through a pad of celite, which was washed several times with methanol. The filtrate was evaporated under vacuum and the product was purified by preparative HPLC.

Method E:

Quinoline (25 µL, 0.21 mmol), palladium on barium sulphate reduced (5%) (360 mg) and the alkyne (1 mmol) were combined in methanol (15 mL) and stirred under atmospheric pressure of hydrogen until the $^{1}$HNMR of the crude showed that the reduction was complete. The catalyst was removed by filtration through a pad of celite, which was washed several times with methanol. The filtrate was evaporated under vacuum and the product was purified by preparative HPLC.

3-Hept-1-enyl-N-(2-hydroxy-1-methyl-ethyl)-benzamide (11)

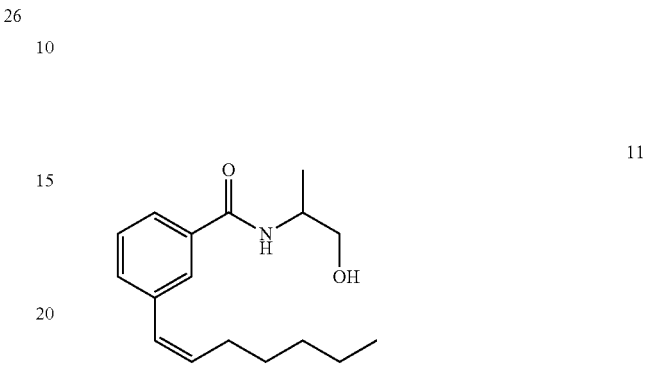

11

Hydrogenation of the alkyne 3 (0.050 g, 0.18 mmol) using method D gave two products, which were separated by preparative reverse-phase HPLC chromatography (55% acetonitrile/45% water 20 min isocratic program), named compound 11 (12 mg) (and the fully reduced compound 3-heptyl-N-(2-hydroxy-1-methyl-ethyl-1)-benzamide (12) (7 mg).

$\delta(^{1}H)$ (CDCl$_3$); 0.88 (3H, t, J 7.0 Hz), 1.30 (3H, d, J 6.8 Hz), 1.33-1.52 (4H, m), 2.26-2.34 (2H, m), 3.66-3.81 (2H, m), 4.25-4.35 (1H, m), 5.69-5.78 (1H, m), 6.22 (1H, bs), 6.43 (1H, d, J 11.7 Hz), 7.26 (1H, s), 7.36 (1H, d, J 7.5 Hz), 7.55-7.65 (1H, m), 7.71 (1H, s).

3-Heptyl-N-(2-hydroxy-1-methyl-ethyl)-benzamide (12)

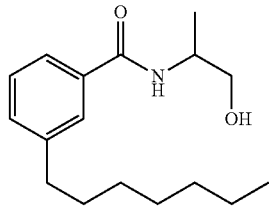

12

$\delta(^{1}H)$ (CDCl$_3$); 0.808 (3H, t, J 6.6 Hz), 1.21 (3H, d, J 6.8 Hz), 1.24 (4H, m), 1.52-1.57 (2H, m), 2.53-2.58 (2H, m), 3.56 (1H, dd, J$_1$ 5.7, J$_2$ 10.9 Hz), 3.69 (1H, dd, J$_1$ 3.6, J$_2$ 10.9 Hz), 4.15-4.23 (1H, m), 6.22 (1H, bd, J 5.6 Hz), 7.25 (2H, d, J 7.7 Hz), 7.50 (1H, m), 7.70 (1H, s).

$\delta(^{13}C)$ (CDCl$_3$); 14.24 (CH$_3$), 17.52 (CH$_3$), 23.01 (CH$_2$), 29.50 (CH$_2$), 29.63 (CH$_2$), 31.77 (CH$_2$), 32.15 (CH$_2$), 36.23 (CH$_2$), 48.57 (CH), 67.49 (CH$_2$), 124.47 (CH), 127.52 (CH), 128.79 (CH), 132.09 (CH), 134.72 (C), 134.72 (C), 143.97 (C), 168.78 (C).

MS (ES) m/z 277 (M+H).

3-(5-Cyano-pent-1-enyl)-N-(2-hydroxy-1-methyl-ethyl)-benzamide (15)

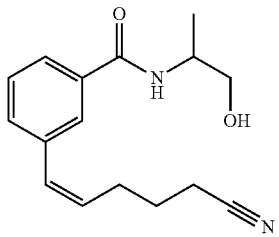

15

Alkyne 7 (0.030 g, 0.1 mmol) was hydrogenated as describe in method E to give 3-(5-cyano-pentyl)-N-(2-hydroxy-1-methyl-ethyl)-benzamide (15 mg) which was purified by reverse-phase HPLC chromatography (20% acetonitrile/80% water 20 min isocratic program).

δ($^1$H) (CDCl$_3$); 1.29 (d, J=6.9 Hz, 3H), 1.82 (m, 2H), 2.38 (t, J=7.0 Hz, 2H), 2.48 (m, 2H), 2.78 (m, 1H), 3.65 (m, 1H), 3.79 (m, 1H), 4.29 (m, 1H), 5.65 (m, 1H), 6.38 (m, 1H), 6.56 (d, J=11.5 Hz, 1H), 7.34-7.44 (m, 2H), 7.64-7.68 (m, 2H).

δ($^{13}$C) (CDCl$_3$); 17.00 (CH$_2$), 17.45 (CH$_3$), 25.67 (CH$_2$), 27.50 (CH$_2$), 48.60 (CH), 67.20 (CH$_2$), 120.00 (C), 125.90 (CH), 127.50 (CH), 129.00 (CH), 130.77 (CH), 131.10 (CH), 132.22 (CH), 135.04 (CH), 137.83 (C), 168.4 (C).

MS (ES) m/z 273 (M+H).

3-(5-Dimethylcarbamoyl-pent-1-enyl)-N-(2-hydroxy-1-methyl-ethyl)benzamide (16)

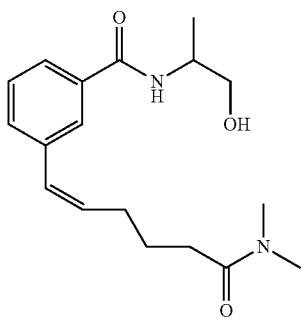 [SMILES: CC(CO)NC(=O)c1cccc(/C=C\CCCC(=O)N(C)C)c1]

16

The alkyne 8 (0.100 g, 0.3 mmol) was synthesized by Lindlar catalyzed reduction using method E to obtain a mixture of 16 and 3-(5-dimethylcarbamoyl-pentyl)-N-(2-hydroxy-1-methyl-ethyl)-benzamide (13) which were separated by reverse-phase HPLC chromatography (20% acetonitrile/80% water 20 min isocratic program) (16, 34 mg).

δ($^1$H) (CDCl$_3$); 1.31 (3H, t, J 6.8 Hz), 1.81-1.91 (2H, m), 2.26-2.39 (4H, m), 2.90 (3H, s); (3H, s); 3.65 (2H, dd, J$_1$ 5.5, J$_2$ 11.2 Hz), 3.83 (2H, dd, J$_1$ 3.2, J$_2$ 11.2 Hz), 4.27-4.30 (1H, m), 5.68-5.77 (1H, m), 6.46 (1H, d, J 11.6 Hz), 7.24-7.33 (1H, m), 7.38 (1H, d, J 7.6 Hz), 7.74-7.79 (2H, m).

δ($^{13}$C) (CDCl$_3$); 16.93 (CH$_3$), 24.80 (CH$_2$), 28.22 (CH$_2$), 32.51 (CH$_2$), 35.73 (CH), 37.45 (CH), 48.32 (CH$_2$), 66.73 (CH$_2$), 126.20 (CH), 126.35 (CH), 128.58 (CH), 129.12 (CH), 131.88 (CH), 132.63 (CH), 134.70 (C), 137.5 (C), 168.00 (C), 173.11 (C).

MS (ES) m/z 319 (M+H).

3-(5-Dimethylcarbamoyl-pentyl)-N-(2-hydroxy-1-methyl-ethyl)-benzamide (13)

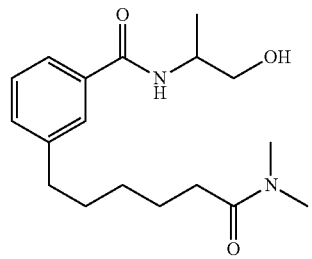

13

δ($^1$H) (CDCl$_3$); 1.28-1.36 (5H, m), 1.64 (2H, m), 2.29 (2H, t, J 7.3 Hz), 2.63 (2H, t, J 7.4 Hz), 2.91 (3H, s), 2.98 (3H), 3.63 (1H, m), 3.78 (2H, m), 4.19-4.30 (2H, m), 6.94 (1H, m), 7.26-7.32 (2H, m), 7.45-7.67 (3H, m).

δ($^{13}$C) (CDCl$_3$); 17.43 (CH$_3$), 25.09 (CH$_2$), 28.81 (CH$_2$), 31.14 (CH$_2$), 33.52 (CH$_2$), 35.54 (CH), 35.89 (CH), 37.80 (CH), 48.55 (CH), 67.08 (CH$_2$), 125.05 (CH), 127.50 (CH), 128.81 (CH), 132.00 (CH), 134.93 (C), 143.13 (C), 168.70 (C), 173.73 (C).

MS (ES) m/z 321 (M+H).

3-(6-Dimethylcarbamoyl-hex-1-enyl)-N-(2-hydroxy-1-methyl-ethyl)-benzamide (17)

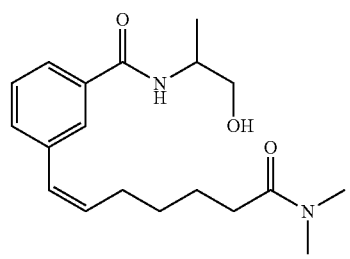

17

3-(6-Dimethylcarbamoyl-hex-1-enyl)-N-(2-hydroxy-1-methyl-ethyl)-benzamide (0.037 g, 0.11 mmol) 17 was synthesized by Lindlar catalyzed reduction using the method D to obtain a mixture of 17 and the saturated compound plus 20% of the trans isomer which were separated by preparative HPLC, unfortunately the separation of the cis and trans isomers was not very successful and the compound 17 (15 mg) was contaminated with some trans isomer (10% trans).

6-[3-(2-Hydroxy-1-methyl-ethylcarbamoyl)-phenyl]-hex-5-enoic acid methyl ester (21)

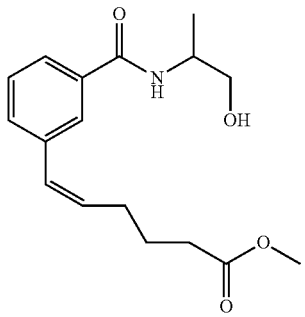

21

6-[3-(2-Hydroxy-1-methyl-ethylcarbamoyl)-phenyl]-hex-5-enoic acid methyl ester (21) (0.100 g, 1.7 mmol) was synthesized by Lindlar catalyzed reduction from the alkyne 20 using method D, to obtain a mixture of 21 and 5% of the trans isomer which was not separated. The mixture was used as a crude.

δ($^1$H) (CD$_3$OD); 1.15 (3H, t, J 6.7 Hz), 1.52-1.71 (2H, m), 2.19-2.29 (4H, m), 3.47-3.56 (2H, m/z), 4.06-4.12 (2H, m), 5.59-5.67 (1H, m), 5.46 (2H, bs), 5.62-5.68 (1H, m), 6.39 (1H, d, J 11.6 Hz), 7.25-7.33 (1H, m), 7.41 (1H, d, J 8.0 Hz), 7.52-7.61 (2H, m).

3-(5-Carbamoyl-pent-1-enyl)-N-(2-hydroxy-1-methyl-ethyl)-benzamide(19)

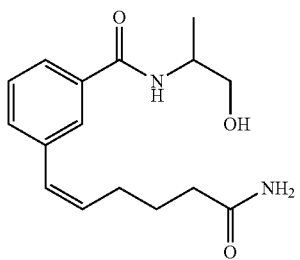

19

21 (0.030 g, 0.10 mmol) was dissolved in 2 mL of ammonia 33% solution in water and stirred at room temperature for 8 h. The solvent was removed and the product was purify by reverse-phase HPLC chromatography (18% acetonitrile/82% water 20 min isocratic program) to give 19 (7 mg).

δ($^1$H)(CDCl$_3$); 1.22 (3H, t, J 6.8.0 Hz), 1.75-1.79 (2H, m), 2.20-2.32 (4H, m), 3.65 (2H, dd, J 5.8, J$_2$ 11.2 Hz), 3.83 (2H, dd, J 2.9, J$_2$ 11.2 Hz), 4.24-4.32 (1H, m), 5.46 (2H, bs), 5.62-5.68 (1H, m), 6.39 (1H, d, J 11.6 Hz), 7.20-7.22 (1H, m), 7.32 (1H, d, J 7.6 Hz), 7.68 (1H, s), 7.74 (1H, d, J 7.7 Hz).

MS (CI) m/z 291 (M+H).

General Method for BER/Ni Hydrogenation

Borohydride polymer-supported (borohydride on amberlite IRA-400 2.5 mmol BH$_4^-$/1 g resin) (BER) (0.750 g) and nickel acetate tetra hydrate (0.046 g, 1.9 mmol) were suspended in 7 mL of methanol, hydrogen was bubbled through the suspension until a black coating of nickel appeared on the resin, then to the mixture under hydrogen the alkyne (1 mmol) was added dissolved in 7 mL of methanol. The mixture was shaken for 9 hours and then filtered. The resin was washed several times with methanol and then the combined filtrate was evaporated under vacuum. The residue was dissolved in an appropriate solvent and filtered though celite to remove the nickel. The product was purified by preparative reverse-phase HPLC chromatography.

3-(4-Dimethylcarbamoyl-but-1-enyl)-N-(2-hydroxy-1-methyl-ethyl)-benzamide (27)

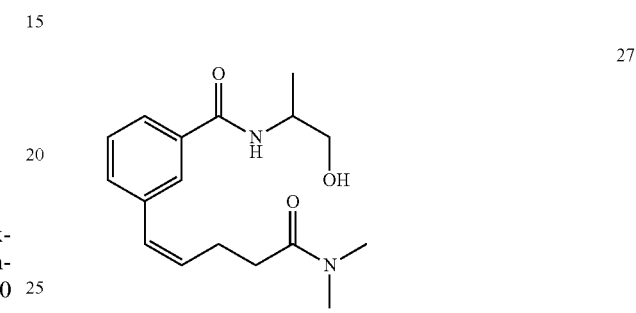

27

Hydrogenation of the alkyne 9 (0.055 g, 0.18 mmol) using BER/Ni catalyst gave 40% 27, 5% of the saturated compound and 55% of starting material. The mixture was separated by reverse-phase HPLC chromatography (20% acetonitrile/80% water 20 min isocratic program) to give 27 (15 mg).

δ($^1$H)(CDCl$_3$); 1.30 (3H, d, J 6.8 Hz), 2.53-2.70 (4H, m), 2.99 (3H, s), 3.07 (3H, s), 3.65-3.69 (1H, m) 3.81-3.95 (1H, m), 3.98-3.40 (1H, m), 4.30-4.31 (1H, m), 5.68-5.77 (1H, m), 6.47 (1H, d, J 11.6 Hz), 7.29 (1H, m), 7.37-7.46 (1H, m), 7.85-7.95 (1H, m), 8.22 (1H, s).

δ($^{13}$C) (CDCl$_3$); 16.84 (CH$_3$), 24.68 (CH$_2$), 32.59 (CH$_2$), 35.89 (CH$_3$), 37.96 (CH$_3$), 48.33 (CH), 66.76 (CH$_2$), 125.67 (CH), 126.90 (CH), 128.71 (CH), 130.03 (CH), 131.15 (CH), 131.88 (CH), 134.46 (C), 136.70 (C), 167.23 (C), 173.30 (C).

N-(2-Hydroxy-1-methyl-ethyl)-3-(5-methylcarbamoyl-pent-1-enyl)-benzamide (18)

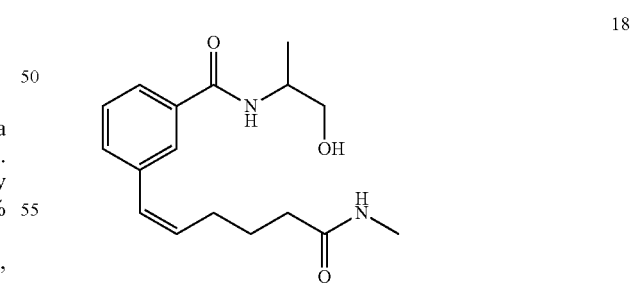

18

The alkyne 22 (0.055 g, 0.16 mmol) was hydrogenated using BER/Ni catalyst to give a mixture of 18 45% and starting material 55%. The mixture was separated by reverse-phase HPLC chromatography (18% acetonitrile/82% water 20 min isocratic program) to give 18 (19 mg).

δ($^1$H) (CDCl$_3$); 1.29 (3H, t, J 6.8.0 Hz), 1.88-1.97 (2H, m), 2.35 (2H, d, J 7.4 Hz), 2.47 (1H, d, J 6.8 Hz), 2.80 (3H, d, J 4.8 Hz); 3.65 (2H, dd, J 5.5, J$_2$ 11.0 Hz), 3.79 (2H, dd, J$_1$ 3.5, J$_2$ 11.2 Hz), 4.23-4.31 (1H, m), 5.73 (1H, bs), 6.53 (1H, bd, J 6.2 Hz), 7.33 (1H, t, J 7.7 Hz), 7.45 (1H, d, J 7.7 Hz), 7.69 (1H, d, J 7.8 Hz), 7.76 (1H, s).

$\delta(^{13}C)$ (CDCl$_3$); 17.07 (CH$_3$), 18.91 (CH$_2$), 24.44 (CH$_2$), 26.32 (CH$_3$), 35.19 (CH$_2$), 48.19 (CH), 66.87 (CH$_2$), 1224.23 (C), 126.41 (CH), 128.57 (CH), 129.99 (CH), 134.31 (CH), 134.59 (C), 167.00 (C), 178.00 (C).

3-(5-Dimethylcarbamoyl-pent-1-enyl)-N-(2-fluoro-ethyl)-benzamide (28)

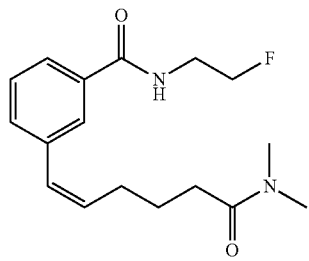

Hydrogenation of 3-(5-dimethylcarbamoyl-pent-1-ynyl)-N-(2-fluoro-ethyl)benzamide (26) (0.040 g, 0.13 mmol) using BER/Ni catalyst gave 40% 28, and 55% of starting material. The mixture was separated by reverse-phase HPLC chromatography (30% acetonitrile/70% water 20 min isocratic program) to give 3-(5-dimethylcarbamoyl-pent-1-enyl)-N-(2-fluoro-ethyl)-benzamide 28 (5 mg).

$\delta(^1H)$ (CDCl$_3$); 1.80-1.89 (2H, m), 2.31-2.41 (4H, m), 2.88 (3H, s), 2.97 (3H, s), 3.68-3.72 (1H, m), 3.74 (1H, dd, J$_1$ 5.4, J$_2$ 10.7 Hz), 3.82 (1H, dd, J$_1$ 5.4, J$_2$ 10.7 Hz), 5.72-5.78 (1H, m), 6.43 (1H, d, J 11.7 Hz), 7.31 (1H, d, J 7.7 Hz), 7.40 (1H, t, J 7.7 Hz), 7.81 (1H, d, J 7.9 Hz), 8.02 (1H, s).

N-Cyclopropyl-3-(5-dimethycarbamoyl-pent-1-enyl)-benzamide (29)

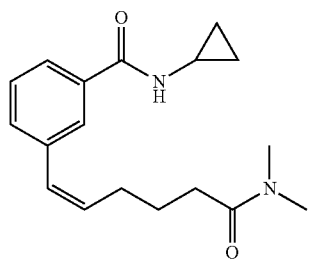

Hydrogenation using BER/Ni catalyst overnight of 3-(N-cyclopropyl-3-(5-dimethylcarbamoyl-pent-1-ynyl)benzamide (25) (0.040 g, 0.13 mmol) gave 90% 28, and 10% of starting material. The mixture was separated by reverse-phase HPLC chromatography (30% acetonitrile/70% water 20 min isocratic program) to give N-cyclopropyl-3-(5-dimethycarbamoyl-pent-1-enyl)-benzamide (10 mg).

$\delta(^1H)$ (CDCl$_3$); 0.64-0.69 (2H, m), 0.78-0.84 (2H, m), 1.78-1.83 (2H, m), 2.28-2.36 (4H, m), 2.88 (3H, s), 2.89-2.93 (1H, m), 2.97 (3H, s), 5.65-5.75 (1H, m), 6.43 (1H, d, J 11.7 Hz), 7.33 (1H, t, J 7.8 Hz), 7.44-7.49 (1H, m), 7.63-7.72 (1H, m), 7.84 (1H, s).

Validation as CB1 Agonists with Peripheral Action

In Vitro Radioligand Binding Studies

Radioligand binding assays [Ross, R. A. et al, *Br. J. Pharmacol.* 1999, 128, 735-743] are carried out with the CB$_1$ receptor antagonist [3H]SR141716A (0.5 nM) or [3H] CP55940 (0.5 nM) in brain and spleen membranes. Assays are performed in assay buffer containing 1 mg/mL BSA, the total assay volume being 500 µL. Binding is initiated by the addition of membranes (100 µg). The vehicle concentration of 0.1% DMSO is kept constant throughout. Assays are carried out at 37° C. for 60 minutes before termination by addition of ice-cold wash buffer (50 mM Tris buffer, 1 mg/mL BSA) and vacuum filtration using a 12-well sampling manifold (Brandel Cell Harvester) and Whatman GF/B glass-fibre filters that had been soaked in wash buffer at 4° C. for 24 hours. Each reaction tube is washed five times with a 4-mL aliquot of buffer. The filters are oven-dried for 60 minutes and then placed in 5 mL of scintillation fluid (Ultima Gold XR, Packard), and radioactivity quantitated by liquid scintillation spectrometry. Specific binding is defined as the difference between the binding that occurred in the presence and absence of 1 µM unlabelled ligand and is 71% and 40% of the total radio-ligand bound in brain and spleen respectively. The concentrations of competing ligands (test compounds) to produce 50% displacement of the radioligand (IC50) from specific binding sites is calculated using GraphPad Prism (GraphPad Software, San Diego). Inhibition constant (Ki) values are calculated using the equation of Cheng & Prusoff [Cheng, Y. and Prusoff, W. H., *Biochem. Pharmacol.* 1973, 22, 3099-3108].

In Vitro Cannabinoid Receptor Modulating Activity

Compounds are evaluated for cannabinoid modulation potential using a mouse vas deferens preparation [Ward S, Mastriani D, Casiano F and Arnold R (1990) *J Pharmacol Exp Ther* 255:1230-1239] which provides evidence for CB agonism, rather than simple receptor binding which does not always reflect agonist potential. Compound (16) showed significant effects in this system (FIG. 1) with an IC$_{50}$ of ~1 nM compared to the known full agonist R(+) WIN55,212 (IC$_{50}$ ~5 nM). This was inhibited by the selective CB$_1$ antagonist SR141716A indicating that the observed contraction was mediated via the peripheral CB$_1$ receptor.

In Vivo Peripheral CB$_1$ Receptor Activation

Upper Gastrointestinal Transit

Gastrointestinal transit is measured using the charcoal method. Mice receive orally 0.1 mL (10 g/mouse) of a black marker (10% charcoal suspension in 5% gum arabic), and after 20 minutes the mice are killed by asphyxiation with CO$_2$ and the small intestine removed. The distance traveled by the marker is measured and expressed as a percentage of the total length of the small intestine from pylorus to caecum [Izzo, A. A. et al, *Br. J. Pharmacol.* 2000, 129, 1627-1632]. Cannabinoid agonists are given 30 min before charcoal administration.

Colonic Propulsion Test

Distal colonic propulsion is measured according to Pinto et al [*Gastroenterology* 2002, 123, 227-234]. Thirty minutes after the administration of cannabinoid drugs, a single 3 mm glass bead is inserted 2 cm into the distal colon of each mouse. The time required for expulsion of the glass bead was determined for each animal. The higher mean expulsion time value is an index of a stronger inhibition of colonic propulsion.

Psychotrophic Activity of Peripherally Active Cannabinoids

Many CB$_1$ agonists are known to induce psychotrophic associated "tetrad effects" due to central binding to CB receptors [Howlett, A. C. et al, International Union of Pharmacology. XXVII, Pharmacol. Rev. 2002, 54, 161-202]. Studies were undertaken to investigate whether the compounds of the present invention also bound to central $CB_1$ receptors. This is assessed by measuring the ability of the compounds to induce sedation, ptosis, hypomotility, catalepsy and hypothermia in normal mice [Brooks, J. W. et al, *Eur. J. Pharmacol.* 2002, 439, 83-92], following i.v., i.p. and oral administration.

Determination of Compound Brain Levels

Quantitation of Permeability into Brain and Spinal Cord

Brain/spinal cord penetration of the compounds may be measured directly as follows. Brain and spinal cord uptake in anaesthetised rat is measured using the standard method set forth in Ohno et al [Ohno, K. et al, *Am. J. Physiol* 1978, 235, H299-H307]. In brief, the compound is injected intravenously (femoral), as either single bolus or stepped infusion. Several plasma samples (femoral artery) are taken to calculate the plasma concentration over time (integral, area under the curve). Terminal brain and spinal cord samples are taken to measure brain penetration (correcting for compound in residual blood by either saline washout or by measuring contained blood volume using short circulation of an inert low permeability marker such as [$^{14}$C] sucrose). PS (cm·s–1), is equal to Cbrain/integral Cplasma, where PS=permeability× surface area (cm$^2$) product for brain uptake, and C is concentration. Alternatively, a steady state tissue/plasma ratio is measured as a more approximate index, again with blood washout or correction. Comparison is made with control compounds known to have low permeability across the BBB, e.g. radiolabelled sucrose or insulin, run under identical conditions.

Preliminary Characterization of the Biology of $CB_1$ Agonism

Nociceptive Activity of Peripherally Active Cannabinoids

There is evidence for $CB_1$ mediated nociception in the periphery [Fox, A. et al, *Pain* 2001, 92, 91-100]. Studies on partial sciatic nerve ligation were therefore undertaken in rats and knockout mice.

Assessment of Spasticity

Further studies were undertaken using cannabinoid knockout mice, including $CB_1$, $CB_2$, VR-1, FAAH and conditional $CB_1$ knockout mice. Spasticity may be induced in ABH (significant spasticity occurs in 50-60% of animals in 80 days after 3-4 disease episodes[1]) or ABH.$CB_1$–/– (significant spasticity occurs in 80-100% of animals in 30-days after 1-2 disease episodes). Compounds are injected initially intravenously (to limit first pass effects), i.p. or orally. Spasticity is assessed (n=6-7/group) by resistance to hindlimb flexion using a strain gauge [Baker, D. et al, *Nature* 2000, 404, 84-87]. Animals serve as their own controls and will be analysed in a pairwise fashion. To reduce the number of animals, effort and expense, following a drug-free period (spasticity returns within 24 h) these animals receive different doses and or vehicle. Low doses of $CB_1$ agonists and CNS active CP55,940, as control, are locally (subcutaneous, intra-muscularly) administered into spastic ABH mice and the lack of activity in a contralateral limb analysed [Fox, A. et al, *Pain* 2001, 92, 91-100]. Expression of $CB_1$ in the peripheral nervous system, including dorsal root ganglia, a non-CNS site for CB-mediated nociception can be removed using peripherin-Cre transgenic mouse [Zhou, L. et al, *FEBS Lett.* 2002, 523, 68-72]. These conditional KO mice are maintained on the C57BL/6 background. These mice develop EAE following induction with myelin oligodendrocyte glycoprotein residues 35-55 peptide [Amor, S. et al, *J. Immunol.* 1994, 153, 4349-4356].

In Vivo Evaluation in Normal and CREAE Mice

A CNS excluded compound provides a tool for examining if a component of a cannabinoid anti-spastic effect is mediated via peripheral CB receptors. Compound (16) was examined for CNS effects in normal mice as shown in FIGS. 2 and 3. At a dose of 1 mg/kg no hypothermia or hypomotility was observed. In CREAE mice a marked effect on spasticity was noticed (FIG. 4) providing strong evidence that a selective inhibition of spasticity is achievable without producing CNS effects. As stated above there is no established role for peripheral cannabinoid receptors in the control of spasticity, however, spasticity is likely to be a product of nerve damage in the spinal cord, at least in EAE, [Baker, D. et al, *FASEB J.* 2001, 15, 300-302; Baker, D. et al, *J Neuroimmunol.* 1990, 28, 261-270] and aberrant signals to and from the musculature are likely, at least in part to contribute to the muscle spasms occurring in spasticity.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

We claim:

1. A compound of formula I, or a pharmaceutically acceptable salt thereof,

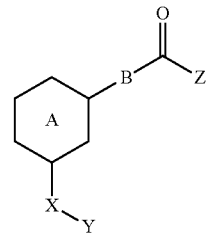

wherein

Z is selected from OH, NHCH$_2$CH$_2$F, NHCH(Me)CH$_2$OH and NHCH$_2$CH$_2$OH;

X is an alkenylene or alkynylene group, each of which may be optionally substituted by one or more substituents selected from alkyl, COOH, CO$_2$-alkyl, akenyl, CN, NH$_2$, hydroxy, halo, alkoxy, CF$_3$, and nitro;

Y is a polar functional group selected from OH, NO$_2$, CN, COR$^3$, COOR$^3$, NR$^3$R$^4$, CONR$^3$R$^4$, SO$_3$H, SO$_2$—R$^3$, SO$_2$NR$^3$R$^4$ and CF$_3$, where each of R$^3$ and R$^4$ is independently H or a hydrocarbyl group;

A is phenyl or pyridyl; and

B is (CH$_2$)$_n$ where n is 0;

with the proviso that:

when A is phenyl, and Z is OH, X—Y is other than C≡C—(CH$_2$)$_2$OH, C≡C—(CH$_2$)$_2$OH, C≡C—(CH$_2$)$_2$CO$_2$Me.

2. A compound according to claim 1 wherein Y is selected from CN, OH, COOR$^3$, SO$_2$NR$^3$R$^4$, CONR$^3$R$^4$, where each of R$^3$ and R$^4$ is independently H or a hydrocarbyl group.

3. A compound according to claim 1 wherein each of R$^3$ and R$^4$ is independently H, an alkyl group, an aryl group, or a cycloalkyl group, each of which may be optionally substituted.

4. A compound according to claim 1 wherein Y is selected from OH, CN, COOR$^3$, CONR$^3$R$^4$, where each of R$^3$ and R$^4$ is independently H or an optionally substituted alkyl group.

5. A compound according to claim 1 wherein Y is selected from OH, CN, COOMe, COOH, CONH$_2$, CONHMe and CONMe$_2$.

6. A compound according to claim 1 wherein X—Y is selected from

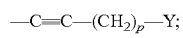

and

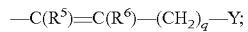

wherein each of $R^5$ and $R^6$ is independently H or alkyl, and each of p and q is independently 2, 3, or 4.

7. A compound according to claim 1 wherein X—Y is selected from

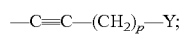

and

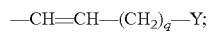

wherein each of p and q is independently 2, 3 or 4.

8. A compound according to claim 6 wherein X—Y is

9. A compound according to claim 1 wherein A is phenyl.

10. A compound which is selected from the group consisting of

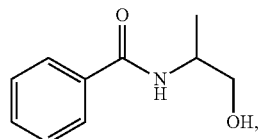

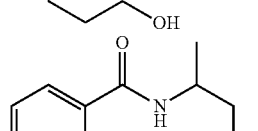

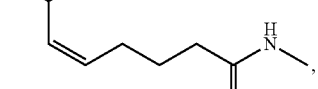

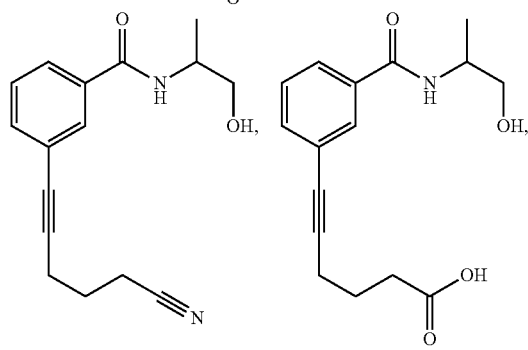

-continued

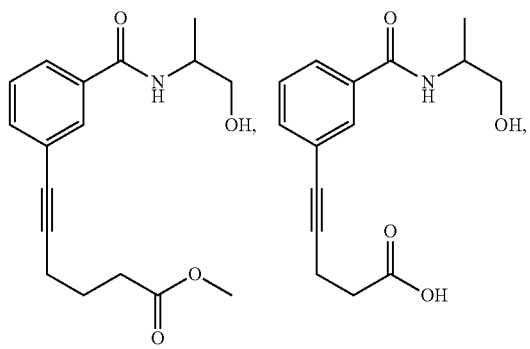

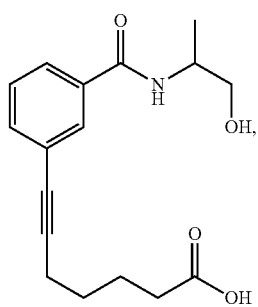

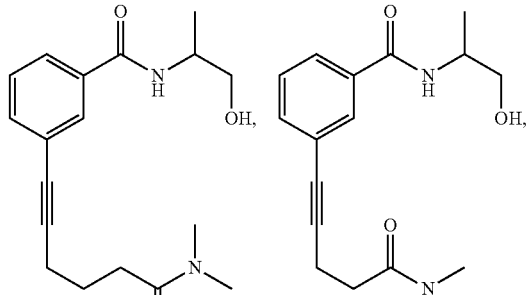

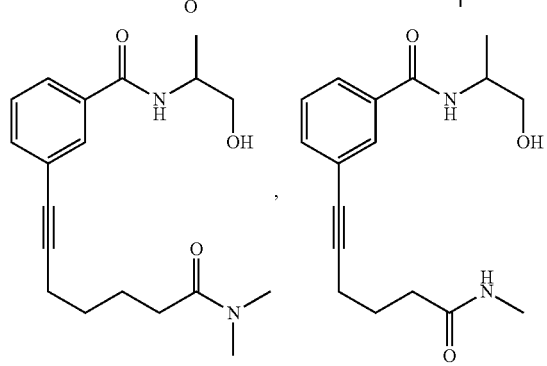

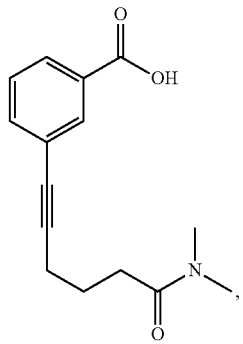

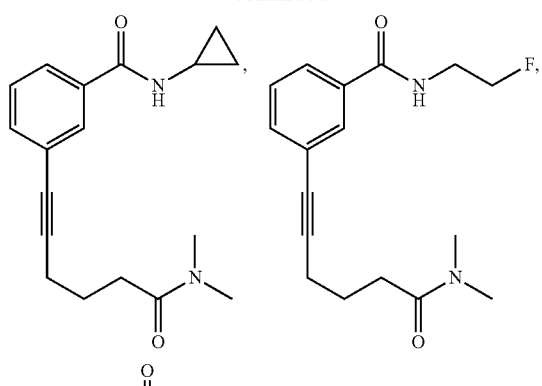
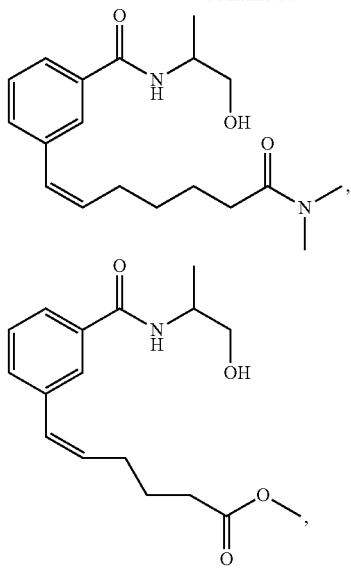
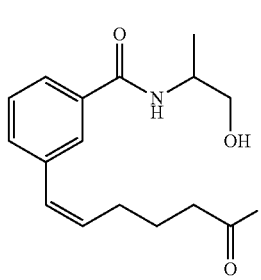
11. The compound of claim 10 which is
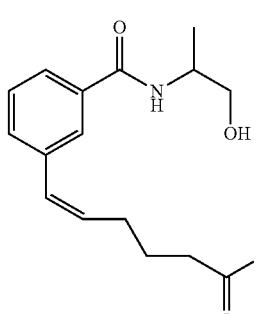
12. The compound of claim 11 which is in the form of a racemic mixture.

13. A compound according to claim 10 selected from the following:
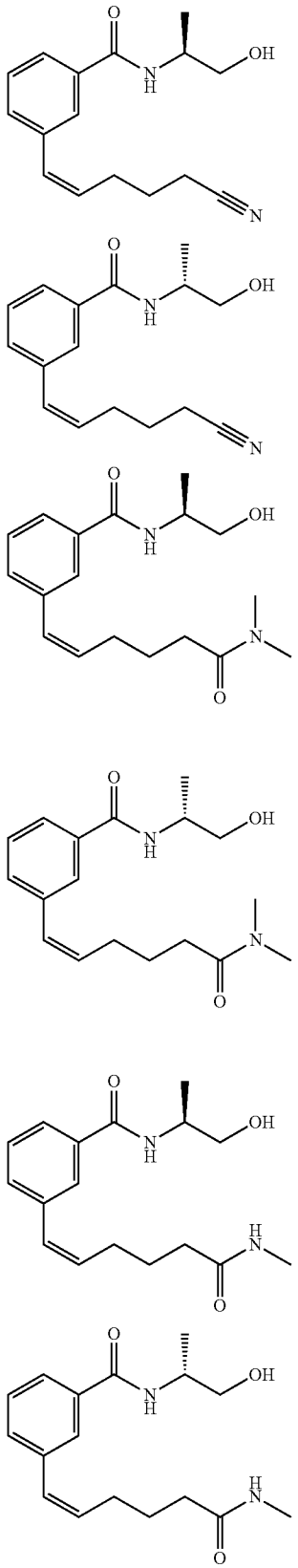
14. The compound according to claim 11 selected from the following:
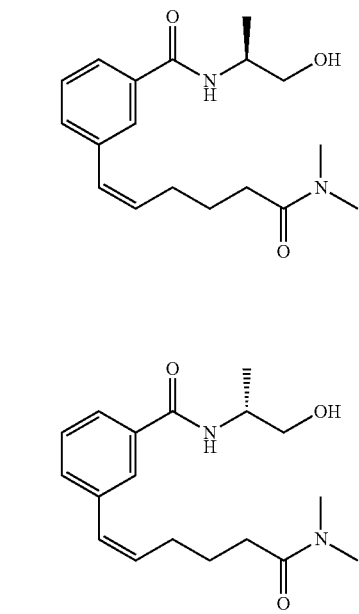
15. A compound according to claim 13 selected from the following:
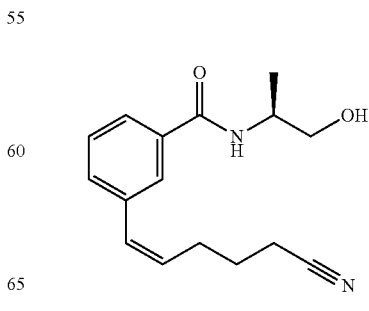

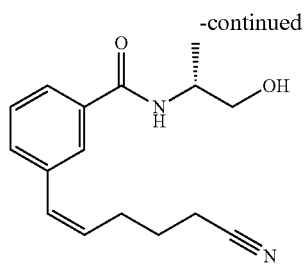
16. A compound according to claim 13 selected from the following:
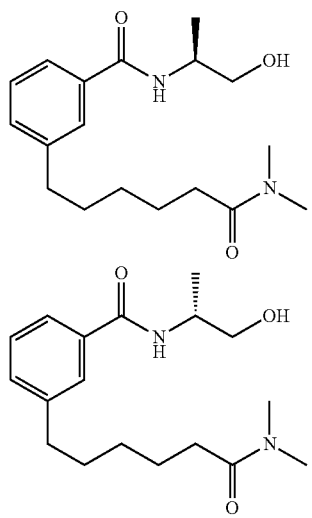
17. A compound according to claim 13 selected from the following:
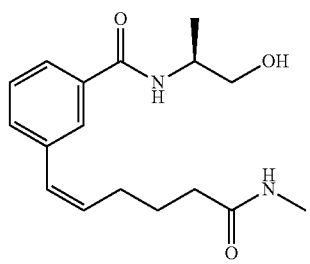
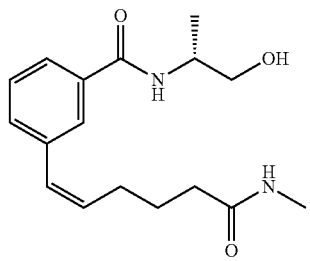
* * * * *